US008808706B2

(12) United States Patent
Duncan et al.

(10) Patent No.: US 8,808,706 B2
(45) Date of Patent: Aug. 19, 2014

(54) *ARTHROSPIRA*-BASED COMPOSITIONS AND USES THEREOF

(75) Inventors: Kelvin Winston Duncan, Avonhead (NZ); Peter Owen Johnston, Carrara (NZ); Ashley Michael Brown, Glebe (AU)

(73) Assignee: Biovite Australia Pty. Ltd. (AU)

( * ) Notice: Subject to any disclaimer, the term of this patent is extended or adjusted under 35 U.S.C. 154(b) by 1433 days.

(21) Appl. No.: 11/718,247

(22) PCT Filed: Nov. 3, 2005

(86) PCT No.: PCT/AU2005/001693
§ 371 (c)(1),
(2), (4) Date: Jan. 27, 2009

(87) PCT Pub. No.: WO2006/047830
PCT Pub. Date: May 11, 2006

(65) Prior Publication Data
US 2009/0123429 A1    May 14, 2009

(30) Foreign Application Priority Data
Nov. 3, 2004  (AU) ............................... 2004906317

(51) Int. Cl.
*A01N 65/00* (2009.01)
(52) U.S. Cl.
USPC ................... 424/195.17; 424/93.4; 424/257.1
(58) Field of Classification Search
None
See application file for complete search history.

(56) References Cited

U.S. PATENT DOCUMENTS

| | | | |
|---|---|---|---|
| 3,403,471 A | | 10/1968 | Clement et al. |
| 5,443,844 A | * | 8/1995 | McDaniel ..................... 424/484 |
| 2003/0017558 A1 | * | 1/2003 | Pham et al. ................... 435/134 |

FOREIGN PATENT DOCUMENTS

| | | | |
|---|---|---|---|
| DE | 1767269 | | 8/1971 |
| DE | 10059107 A1 | | 6/2001 |
| DE | 10059107 A1 | * | 6/2001 |
| EP | 0629397 A1 | | 6/1994 |
| FR | 90002 E | | 9/1967 |
| JP | 52031836 | | 3/1977 |
| JP | 54140737 | | 3/1977 |
| JP | 7145067 A | | 6/1995 |
| JP | 52021336 | | 2/1997 |
| JP | 09067265 | | 3/1997 |
| JP | 2001224332 | | 8/2001 |
| MD | 2516 | | 8/2004 |
| NZ | 382013 | | 6/1999 |
| WO | 9825470 A1 | | 6/1998 |
| WO | 9825471 | | 6/1998 |
| WO | 98/54987 | | 12/1998 |

OTHER PUBLICATIONS

Ozdemir et al., Phytotherapy Research, 2004, vol. 18, p. 754-757.*
Srinivas et al., Plant Food and human Nutrition, 1999, vol. 54, p. 89-92.*
Alberti et al., International Journal of Pharmaceutics, 2001, vol. 219, p. 11-19.*
Scheldman et al., FEMS Microbiology Letters, 1999, vol. 172, p. 213-222.*
Wikipedia: "*Spirulina*" Wikipedia, [Online] Aug. 11, 2009, XP002541990 Internet Retrieved from the Internet: URL:http://en.wikipedia.org/wiki/Spirulina_(dietary_supplement)> [retrieved on Aug. 18, 2009].
Hidenori Shimamatsu: "Mass production of *Spirulina*, an edible microalga" Hydrobiologia, Kluwer Academic Publishers, DO, vol. 512, No. 1-3, Jan. 1, 2004, pp. 39-44, XP019244647 ISSN: 1573-5117.
Kontoyiannis D P et al: "Combination chemotherapy for invasive fungal infections: What laboratory and clinical studies tell us so far" Drug Resistance Updates 200310 DB, vol. 6, No. 5, Oct. 2003, pp. 257-269.
Kontoyiannis D P et al: "Toward more effective antifungal therapy: The prospects of combination therapy" British Journal of Haematology 200407 GB, vol. 126, No. 2, Jul. 2004, pp. 165-175.
Baranowski, JD, Dominguez, CA and Magarelli, PC, Effects of drying on selected qualities of *Spirulina platensis* protein, J. Agric. Food Chem., 1984, 32(6), 1385-1387 (Abstract only).
Desmorieux, H and Hernandez, F, Biochemical and physical criteria of *Spirulina* after different drying processes, Drying 2004—Proceedings of the 14th International Drying Symposium, Sao Paolo, Brazil, Aug. 22-25, 2004, vol. B, 900-907.
Manen, Jean-François and Falquet, Jacques, 'The cpcB-cpcA locus as a tool for the genetic characterization of the genus *Arthrospira* (Cyanobacteria): evidence for horizontal transfer', Int'l. Journal of Systematic and Evolutionary Microbiology, 2002, vol. 52, pp. 861-867; DOI: 10.1099/ijs.0.01981-0. 7 pages.
The Korean Intellectual Property Office Office Action [Notice of Preliminary Rejection] issued on Aug. 27, 2012; Biovite Australia Pty. Ltd.; 3 pages.
Ayehunie S. et al, "Inhibition of HIV-1 replication by an aqueous extract of *Spirulina platensis* (*Arthrospira platensis*)", Journal of Acquired Immune Deficiency Syndromes and Human Retrovirology, 1998, vol. 18, pp. 7-12.
Baranowski. J.D. et al, "Effects of drying on selected qualities of *Spirulina platensis* protein.", 1984, J. Agric. Food Chem., vol. 32 (6), pp. 1385-1387.
Belay A., "The potential application of *Spirulina* (*Arthrospira*) as a nutritional and therapeutic supplement in health management", 2002, The Journal of the American Nutraceutical Assoc., vol. 5, No. 2, pp. 27-48.
Blinkova L.P. et al, "Biological activity of *Spirulina*", 2001, Zh. Mikrobiol. Epidemiol. Immunobiol., vol. 2, pp. 114-118.

(Continued)

*Primary Examiner* — Kade Ariani
(74) *Attorney, Agent, or Firm* — Schmeiser, Olsen & Watts LLP

(57) ABSTRACT

The present invention concerns a composition comprising physiologically stressed *Arthrospira maxima* for use as a biocide and/or therapeutic. The invention also concerns a method for preventing or treating an infection or infestation of a subject by an organism, wherein the method comprises the step of administering to the subject an effective amount of a composition comprising physiologically stressed *Arthrospira*.

24 Claims, 18 Drawing Sheets

(56) References Cited

OTHER PUBLICATIONS

Blinkova L.P. et al, "Detection of bioactive compounds with antagonistic and stimulation activity in *Spirulina platensis*", 2002, Zhurnal Mikrobioligii, Epidemiologii i Immunobiologii, vol. 5, pp. 11-15.
Brinen L. S. et al, "Paracyclophanes from Blue-Green Algae", 1990, J. Am. Chem. Soc., vol. 112, pp. 4061-4063.
Ciferri O. et al, "Genetic and biochemical studies of *Spirulina*: a possible source of alimentary protein", 1983, Rivista Di Biologia, vol. 76, No. 2, pp. 217-224.
De Philippis, R. et al, "Glycogen and poly-beta-hydroxybutyrate synthesis in *Spirulina maxima*.", 1992, The Journal of General Microbiology, vol. 138 (8), pp. 1623-1628.
Entzeroth M. et al., "A Herbicidal Fatty Acid Produced by *Lyngbya aestuarii*", 1985, Phytochemistry, vol. 24. No. 12, pp. 2875-2876.
Falquet J., "The Nutritional Aspects of *Spirulina*", 1997, pp. 1-23.
Gallon J.R. et al., 'Cyanobacterial biotechnology: ancient organisms and the oldest science', 1991, Genetic Engineer. & Biotechnol., vol. 11, No. 5, pp. 15-17.
Gerwick W.H. et al., "Two Malyngamides From the Caribbean Cyanobacterium *Lyngbya majuscula*", 1987, Phytochemistry, vol. 26, No. 6, pp. 1701-1704.
Gorobets, O.B. et al., "Effect of microalgae on viability of microorganisms in the natural and artificial environment", Zh. Mikrobiol. Epidemiol. Immunobiol., Jan.-Feb. 2001, (1), pp. 104-108.
Gorobets, O.B. et al., "Stimulating and inhibiting effect of *Spirulina platensis* on microorganisms", 2001, Zh. Mikrobiol. Epidemiol. Immunobiol., Nov.-Dec., (6), pp. 20-4.
Gorobets, OB et al., "Action of *Spirulina platensis* on bacterial viruses", 2002, Zh. Mikrobiol. Epidemiol. Immunobiol., Nov.-Dec., (6), pp. 18-21.
Hernandez-Corona A. et al., 'Antiviral activity of *Spirulina maxima* against herpes simplex virus type 2', 2002, Antiviral Research, vol. 56, No. 3, pp. 279-285.
Jensen G.S. et al., "Blue-Green Algae as an Immuno-Enhancer and Biomodulator", Applied Health's Blue-Green Algae Report, 2004.
Jorjani G.H. et al., 'Antibacterial activities of *Spirulina platensis*', 1978, Majallah Ilmy Puzshky Danishkadah Jundi Shapur, vol. 1, No. 1, pp. 14-18.
Klochenko P.D. et al., 'Antifungal activity of freshwater cyanobacteria', 2001, Archiv Fuer Hydrobiologie, Supplement, vol. 140, pp. 143-149.
Martinez Nadal N.G., "Sterols of *Spirulina maxima*", 1971, Phytochemistry, vol. 10, pp. 2537-2538.
Ozdemir G. et al., "Antibacterial Activity of Volatile Component and Various Extracts of *Spirulina plantensis*", 2004, Phytotherapy Research, Phytother. Res., 18, pp. 754-757.
Padula M. et al., "Photodynamic action of phycocyanin: damage and repair.", 1996, Journal of Photochemistry and Photobiology B: Biology; vol. 32, (1-2): 19-26.
Pang, Q. et al., "Radioprotective effect of extract from *Spirulina platensis* in mouse bone marrow cells studied by using the micronucleus test." 1989, Toxicology Letters, vol. 48: 165-169.
Pascaud M., 'The essential polyunsaturated fatty acids of *Spirulina* and our immune response', 1993, Bulletin de l'institut Oceanographique, Monaco, No. special 12, pp. 49-57.
Sanchez M. et al., '*Spirulina* (*Arthrospira*): An edible microorganism: A review', 2003, Universitas Scientarium (Pontificia Universidad Javeriana, Facultad de Ciencias, vol. 8, No. 1, 2003, pp. 7-24.
Seshadri C.V. et al., 'Beta-Carotene Studies in *Spirulina*', 1991, Bioresource Technology, vol. 38, pp. 111-113.
Shih, S-R. et al, "Inhibition of enterovirus 71-induced apoptosis by allophycocyanin isolated from a blue-green alga *Spirulina platensis*.", 2003, Journal of Medical Virology, vol. 70 (1), pp. 119-125.
Tadros M.G. et al., 'Yield and quality of Cyanobacteria *Spirulina maxima* in continuous culture in response to sodium chloride', 1995, Appl. Biochem. Biotechnol., vol. 51-52, pp. 275-281.
Tomaselli, L. et al., "Physiology of stress response in *Spirulina* spp." 1993, Bulletin de l'Institut Oceanographique (Monaco), vol. 0, No. Spec. Issue 12, pp. 65-75.
Zhang H-Q. et al., 'Chemo- and radio-protective effects of polysaccharide of *Spirulina platensis* on hemopoietic system of mice and dogs', 2001, Acta Pharmacologica Sinica, vol. 22, No. 12, pp. 1121-1124.
Unidentified author—"New Clinical Research with *Spirulina*".
Ballot, A., "Cyanobacteria in Kenyan Rift Valley lakes—a biological and toxicological study", Dissertation, Chapter 13, Feb. 21, 2004. Retrieved from the internet on Aug. 28, 2012 at http://www.diss.fuberlin.de/diss/servlets/MCRFileNodeServlet/FUDISS_derivate_000000001245/13_chapter13.pdf?hosts=.
Tomaselli, Luisa "Morphology, Ultrastructure and Taxonomy of *Arthrospira* (*Spirulina*) *maxima* and *Arthrospira* (*Spirulina*) *platensis*"; "Chapter 1" In: Avigad Vonshak: *Spirulina platensis* (*Arthrospira*): Physiology, Cell-biology and Biotechnology, 1997, pp. 1-15.
Canadian Application No. 2,627,187 Office Action dated Oct. 29, 2012. 5 pages.
Application No. EP 05 799 363.6, European Search Report dated Oct. 14, 2009.
Application No. EP 12 15 7835, European Search Report dated Aug. 28, 2012.

\* cited by examiner

*Aspergillus niger*
Life stream 12.5% original powder

*T. rubrum*

3:00 – Siam algae Co (12.5%)
6:00 – Life Stream (12.5%)
9:00 – China Spirulina (12.5%)

Inhibitory Test
*(Pathogen: Candida albicans)*

Tripod lab cream (clotrimazole 1% + tea tree oil) – 10mm

Inhibitory Test
*(Pathogen: Trichophyton rubrum)*

12:00 - AMYCOT® 12.5% cream – 8mm
3:00 - Tinaderm (tolnaftate 2%) – 0mm
6:00 - Placebo – 0mm
9:00 - Daktarin (miconazole 2%) – 15mm Inhibitory Test
*(Pathogen: Candida albicans)*

12:00 - AMYCOT® 12.5% cream – 2mm
3:00 - Tinaderm (tolnaftate 2%) – 3mm
6:00 – placebo – 0mm
9:00 - Daktarin (miconazole 2%) – 15mm

FIG. 16
Inhibitory Test
*(Pathogen: Trichophyton mentagrophytes)*

50% AMYCOT® 12.5% cream + 50% Daktarin (miconazole 2%) – 10mm
Resolve Tinea (miconazole 2%) – 10mm
Resolve Balm (miconazole 2%) – 7mm
Resolve Plus (miconazole 2%) – 11mm

*(NOTE: combined cream is effectively 6% AMYCOT® + 1% miconazole)*

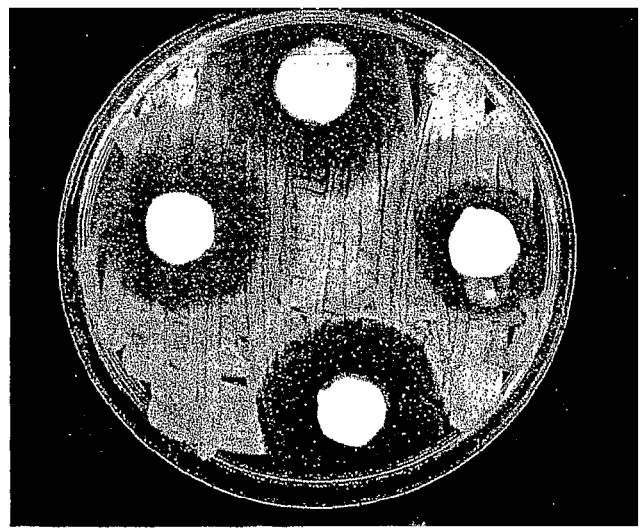

FIG. 17
*(Pathogen: Candida albicans)*

12:00 - AMYCOT® + Daktarin – 10mm
*Resolve* tinea (miconazole 2%) – 6mm
Resolve Balm (miconazole 2%) – 7mm
Resolve Plus (miconazole 2%) – 11mm

*(NOTE: combined cream is effectively 6% AMYCOT® + 1% miconazole)*

Inhibitory Test
*(Pathogen: Trichophyton mentagrophytes)*

12:00 - AMYCOT® 12.5% cream – 1mm
3:00 - AMYCOT 12% + clotrimazole 10% – 13mm
6:00 - AMYCOT 12% + terbinafine1% – 1mm
9:00 - AMYCOT 12% + tolnaftate 10% – 1mm Inhibitory Test
*(Pathogen: Trichophyton mentagrophytes)*

12:00 - AMYCOT® 12.5% cream – 1mm
3:00 - AMYCOT 12% + clotrimazole 10% – 11mm
6:00 - AMYCOT 12% + terbinafine1% – 2mm
9:00 - AMYCOT 12% + tolnaftate 10% – 4mm

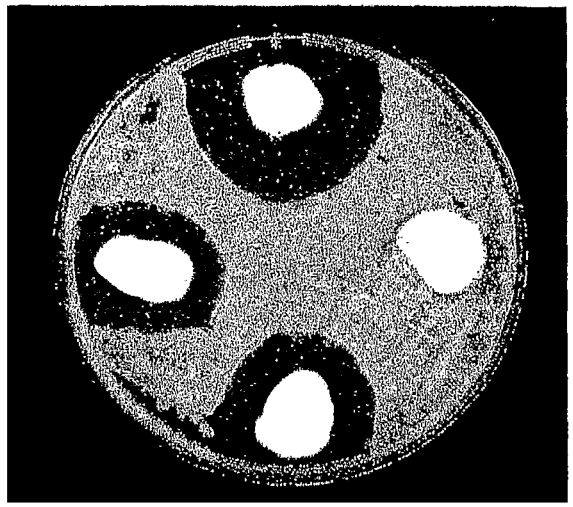

FIG. 20
Inhibitory Test
*(Pathogen: Trichophyton mentagrophytes)*

12:00 - AMYCOT® 12.5% cream + miconazole 2% – 11mm
3:00 – placebo – 0mm
6:00 -Resolve Balm (miconazole 2%) – 7mm
9:00 - Resolve Plus (miconazole 2%) – 7mm

*(NOTE: combined cream is effectively 6% AMYCOT® + 1% miconazole)*

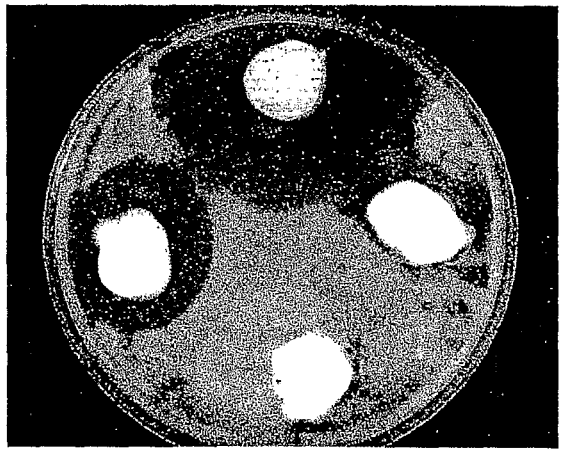

FIG. 21
Inhibitory Test
*(Pathogen: Candida albicans)*

12:00 - 50% AMYCOT® 12.5% cream + 50% Daktarin (miconazole 2%) – 14mm
3:00 – 1% clotrimazole – 4mm
6:00 -10% tolnaftate – 0mm
9:00 – 2%miconazole – 9mm

*(NOTE: combined cream is effectively 6% AMYCOT® + 1% miconazole)*

Fungicidal Test
*(Pathogen: Trichophyton mentagrophytes)*

12:00 - AMYCOT® 12.5% cream – 6mm
3:00 - AMYCOT® 12.5% cream + 1% terbinafine – 6mm
6:00 - AMYCOT® 12.5% cream + 10% tolnaftate – 6mm
9:00 - AMYCOT® 12.5% cream + 10% clotrimazole – 5mm Fungicidal Test
*(Pathogen: Trichophyton rubrum)*

12:00 - AMYCOT® 12.5% cream — 9mm
3:00 - AMYCOT® 12.5% cream + 10% clotrimazole — 7mm
6:00 - AMYCOT® 12.5% cream + 1% miconazole — 8mm
9:00 - placebo — 0mm Fungicidal Test
*(Pathogen: Trichophyton mentagrophytes)*

12:00 - AMYCOT® 12.5% cream — 6mm
3:00 - AMYCOT® 12.5% cream + 1% terbinafine — 5mm
6:00 - AMYCOT® 12.5% cream + 10% tolnaftate — 5mm
9:00 - AMYCOT® 12.5% cream + 10% clotrimazole — 4mm Fungicidal Test
*(Pathogen: Trichophyton mentagrophytes)*

12:00 - AMYCOT® 12.5% cream — 8mm
3:00 - AMYCOT® 12.5% cream + 1% terbinafine — 7mm
6:00 - AMYCOT® 12.5% cream + 10% tolnaftate — 5mm
9:00 - AMYCOT® 12.5% cream + 10% clotrimazole — 4mm Fungicidal Test
*(Pathogen: Trichophyton mentagrophytes)*

12:00 - AMYCOT® 12.5% cream — 9mm
3:00 - AMYCOT® 12.5% cream + 1% terbinafine — 4mm
6:00 - AMYCOT® 12.5% cream + 10% tolnaftate — 5mm
9:00 - AMYCOT® 12.5% cream + 10% clotrimazole — 5mm Fungicidal Test
*(Pathogen: Candida albicans)*

12:00 - AMYCOT® 12.5% cream – 8mm
3:00 - Daktarin (miconazole 2 %) – 0mm
6:00 - Canesten (clotrimazole 1%) – 0mm
9:00 - AMYCOT® 12% + clotrimazole 1% – 5mm Fungicidal Test
*(Pathogen: Trichophyton rubrum)*

12:00 - AMYCOT® 12.5% cream – 6mm
3:00 - 10% clotrimazole – 0mm
6:00 - 10% tolnaftate – 0mm
9:00 - 2% miconazole – 0mm

ARTHROSPIRA-BASED COMPOSITIONS AND USES THEREOF

CROSS REFERENCE TO RELATED APPLICATION

The present application claims priority to PCT/AU2005/001693 filed Nov. 3, 2005, which claims priority from Australian application 2004906317 filed Nov. 3, 2004.

TECHNICAL FIELD

The present invention relates to a composition comprising *Arthrospira* and the use of the composition as a biocide and/or therapeutic.

BACKGROUND ART

*Arthrospira* (formerly known as *Spirulina*) is a cyanobacteria that is grown primarily for use as a food and/or protein source. Therapeutic uses for *Arthrospira* have also been described, including use as an anti-viral agent, anti-cancer agent, reducer of cholesterol, reducer of diabetes, reducer of hypertension and immunomodulator. See, for example, the references cited at the Spirulina Source.com website at www.spirulinasource.com/library.html.

SUMMARY OF THE INVENTION

An object of the present invention is to provide an *Arthrospira* composition for use as a biocide and/or therapeutic.

Physiologically Stressed *Arthrospira* has Biocidal Activity

The present inventors have discovered that *Arthrospira*, when physiologically stressed, produces at least one type of bioactive agent that is active against fungi, bacteria and presumably viruses. *Arthrospira* can be physiologically stressed, for example, by depriving the organism of nutrients or light, or by dehydrating/drying the organism. A sign of an *Arthrospira* filament (trachoma) being "physiologically stressed" is when it enters an anabiotic state, in which state the filament rounds up and a thick mucoid coating is produced. The filament and/or thick mucoid coating is believed by the inventors to contain one or more bioactive agents that protect the organism against predators. One or more of the bioactives may break down the cell wall or exoskeleton of a predatory organism. One or more of the bioactive agents may be, for example, a lytic or modifying agent such as a chitinase, chitosanase or chitin deacetylase, that digests chitin, a chitin derivative (such as chitosan) or other cell wall polymer having, for example, N-acetylglucosamine or D-glucosamine as a polymer subunit. Peptidoglycan of Gram-positive bacteria is one such polymer, comprising N-acetylglucosamine and N-acetylmuramic acid.

According to a first aspect of the present invention, there is provided a composition for digesting or modifying chitin, a chitin derivative or a polymer having N-acetyl-D-glucosamine as a polymer subunit, said composition comprising physiologically stressed *Arthrospira*.

According to a second aspect of the present invention, there is provided a method for digesting or modifying chitin, a chitin derivative or a polymer having N-acetyl-D-glucosamine as a polymer subunit, said method comprising the step of contacting chitin, chitin derivative or a polymer having N-acetyl-D-glucosamine as a polymer subunit with a composition comprising physiologically stressed *Arthrospira*.

The chitin, chitin derivative or polymer can be in any suitable form. The chitin, chitin derivative or polymer can be in a substantially purified form or can be part of an organism such the cell wall of a fungus or Gram-positive bacteria, or part of the exoskeleton of an insect.

According to a third aspect of the present invention, there is provided a method for identifying a bioactive agent from *Arthrospira*, said method comprising the steps of:

(I) combining a composition comprising physiologically stressed *Arthrospira* with at least one test substrate modifiable by a bioactive agent from *Arthrospira*; and (II) assaying for modification of the test substrate.

Any suitable type of test substrate can be used. Assaying for modification of the test substrate can be carried out in any suitable way. High throughput screening, however, is preferred.

Preferably, the bioactive agent is a chitinase, chitosanase or chitin deacetylase and the test substrate is chitin, a chitin derivative or a polymer having N-acetyl-D-glucosamine as a polymer subunit. Preferably, respirometry is used to assay modification (ie. degradation) of the chitin, chitin derivative or other polymer.

The method can further comprise the step of purifying the bioactive agent. Purification can be carried out in any suitable way. The method can also comprise the steps of cloning and expressing the gene/s of the bioactive agent. These steps can be carried out in any suitable way. For instance, the steps can be as described in Maniatis, et al., Molecular Cloning: A Laboratory Manual, Cold Spring Harbor Laboratory, 1982, the entire contents of which are incorporated herein by cross reference.

Use of Physiologically Stressed *Arthrospira* as a Biocide and/or Therapeutic Chitin, chitin derivatives and glucosamine containing polymers are found throughout nature, usually as a component of a cell wall or exoskeleton of, for instance: algae, fungi, protozoans, ciliates, coelenterates, bryozoans, molluscs, annelids, arthropods, branchiopods, phoronida, pogonophora, and bacteria (Gram-positive bacteria and *Rhizobia*).

Hence, physiologically stressed *Arthrospira* having lytic or modifying activity against chitin, chitin derivatives and glucosamine containing polymers is potentially capable of being used as a biocide against a broad range of organisms. "Biocide" as used herein refers to either the killing of an organism or inhibition of the growth or replication of an organism (ie. the organism may not actually be killed). It is to be appreciated that some applications of the biocide will be for therapeutic purposes.

According to a fourth aspect of the present invention, there is provided a composition for use as a biocide and/or therapeutic, said composition comprising an effective amount of physiologically stressed *Arthrospira*.

According to a fifth aspect of the present invention, there is provided a method for preventing or treating an infection or infestation of a subject by an organism, said method comprising the step of administering to the subject an effective amount of a composition comprising physiologically stressed *Arthrospira*.

Preferably, the method comprises the step of identifying a subject in need of such treatment or requiring such prevention.

There is also provided the use of physiologically stressed *Arthrospira* in the preparation of a medicament for the prevention or treatment of an infection or infestation of a subject by an organism.

Surprisingly, the inventors have found that taking *Arthrospira* from its growth environment may be enough for physiological stressing to occur and for inducing expression of one or more bioactive agents having biocidal activity. That is, steps for physiologically stressing *Arthrospira* as taught in the specifications of New Zealand Patents No. 336620 and 336619 need not be carried out and the *Arthrospira* need not be further processed (disrupted, explosively decompressed, potentiated, milled, rehydrated in sodium bicarbonate or freeze dried) in order for there to be biocidal activity.

Furthermore, all commercially available preparations (tablets, capsules and powders) of *Arthrospira* that have thus far been tested by the inventors have been found to have activity against a substrate, and that activity is believed to be indicative of biocidal activity. Such preparations are usually prepared by harvesting the *Arthrospira*, washing and drying the *Arthrospira*, without a step for specifically stressing the organism. In fact, commercial growers of *Arthrospira* tend to minimise stressing of the organism as much as possible as the thick mucoid coating tends to clog machinery for processing the organism.

For any one or more of the compositions described herein, the *Arthrospira* can be any suitable species, or mixture of species or *Arthrospira* variants including, but not limited to, *A. maxima*. It is to be pointed out that *Arthrospira* and *Spirulina* are two separate genera. The separation between these two genera has been repeatedly affirmed on the basis of many characteristics including: helicity and trichome size, cell wall structure and pore pattern, gas vacuoles, thylakoid pattern, trichome motility and fragmentation, GC content, oligonucleotide catalogue of 16S rRNA, and mutations in the cpcB—cpcA locus. See, for instance, J. F. Manen and J. Falquet (2002) "The cpcB—cpcA locus as a tool for the genetic characterization of the genus *Arthrospira* (Cyanobacteria): evidence for horizontal transfer". International Journal of Systematic and Evolutionary Microbiology, Vol 52, 861-867; and, Chapter 1: Morphology, Ultrastructure and Taxonomy of *Arthrospira* (*Spirulina*) *Maxima* and *Arthrospira* (*Spirulina*) *Platensis* by Luisa Tomaselli, of *Spirulina platensis* (*Arthrospira*): Physiology, Cell-biology and Biotechnology. Taylor and Francis. *Avigad Vonshak* (Ed) 1997. The compositions described in this specification exclude species of the *Spirulina* genus.

The composition can comprise intact *Arthrospira* filaments, segments of the filaments, disrupted/lysed segments or extracts/fractions thereof. The composition can comprise *Arthrospira* that is alive or that is not alive. Preferably, the composition comprises disrupted *Arthrospira* filaments and segments.

The *Arthrospira*-based composition can be prepared in any suitable way, provided that the biocidal activity is not compromised. Normally, this would involve the steps of: (I) growing *Arthrospira* in any suitable way; (II) harvesting the grown *Arthrospira* in any suitable way; and (III) drying the *Arthrospira* in any suitable way. Optional steps include: additionally physiologically stressing the *Arthrospira* in any suitable way; disrupting the filaments and segments in any suitable way, sterilising the organism in any suitable way, decolourising the *Arthrospira* in any suitable way, removing or degrading the chlorophyll in any suitable way, and milling the dried *Arthrospira*.

Some of the above steps are described, for example, in the specifications of New Zealand Patents No. 336620 and 336619, the entire contents of which are incorporated herein by cross reference. For example, stressing can be carried out at the time of harvest by either depriving the *Arthrospira* of essential nutrients (nutrient diminution) or light for a period sufficient to stress it but not kill it by management of the growing conditions. Stressing can also be by partial desiccation or by harvesting the *Arthrospira* and keeping it alive in damp conditions until stressed but not dead. For example, *Arthrospira* can be spray dried to form a fine powder of disrupted cells. Spray drying may take place, for example, at 50-190° C. for a few seconds. For example, drying can be carried out in any suitable way, including by cyclonic drying, heat pump drying, heat tube drying, refractory drying or thermal drying under about 67° C. for short periods of time. For example, filaments can be disrupted using milling or explosive decompression as described in New Zealand Patents No. 328013 and No. 328740, the entire contents of which are incorporated herein by cross reference.

The concentration of *Arthrospira* in the composition can vary depending on the application, eg. anywhere from about 0.01% to about 100%. The composition can include any suitable solvent, carrier, base, excipient, filler, binder, plasticiser, emulsifier, stabiliser, lubricant, buffering agent, emollient, solubilising agent, suspending agent, thickener, fragrance, colourant and preservative.

Depending on the intended use, the composition can further comprise one or more actives not derived from *Arthrospira*, such as antimicrobials (e.g. bactericides or antifungals), therapeutic agents (e.g. wound healers, steroids) or general nutrients (e.g. amino acids, vitamins). Such actives are well known in the art.

The composition can be in any suitable form. The composition can be administered or applied in any suitable way. The composition can be a liquid, gel or solid, or a mixture thereof. The composition can be a liquid culture of *Arthrospira* which is applied as a spray. Alternatively, the composition can be a powder which is evenly distributed over a target site by shake or puffer application. The infected or infested subject can be dipped into a bath containing a liquid form of the composition. The composition and method of application or administration can be as described in the specifications of New Zealand Patents No. 336620 and 336619.

For therapeutic use, the composition can be administered or applied, for example, orally, parenterally, by inhalation spray, topically, rectally, nasally, buccally or vaginally. The composition can be a tablet, solution, aerosol, spray, cream, ointment, lotion, emulsion, gel or powder. The composition can be in the form of an *Arthrospira*-impregnated bandage, dressing, adhesive plaster, suppository, pessary or poultice.

Preferably, the biocide is active against fungi, Gram-positive bacteria, protozoa, viruses, crustaceans, acari and insects, some of which are addressed in more detail below.

According to a sixth aspect of the present invention, there is provided a method for preparing an *Arthrospira*-based composition for use as a biocide and/or therapeutic, said method comprising the steps of:
(1) physiologically stressing *Arthrospira*; and
(2) combining the stressed *Arthrospira* of (1) with a suitable carrier, solvent, base or excipient.

According to a seventh aspect of the present invention, there is provided a method for preparing an *Arthrospira*-based composition for use as a biocide and/or therapeutic, said method comprising the steps:
(1) physiologically stressing *Arthrospira* by removing up to about 80% of liquid within which the *Arthrospira* is being grown;

(2) washing the stressed *Arthrospira* in order to remove contaminants;
(3) drying the washed *Arthrospira*; and
(4) combining the washed *Arthrospira* with a suitable carrier, solvent, base or excipient.

Either of the above methods can be used to prepare one or more of the compositions described herein.

Preferably, the above methods exclude specific steps of explosive decompression and/or freeze drying the physiologically stressing *Arthrospira* prior to adding the carrier, solvent, base or excipient.

Use of Physiologically Stressed *Arthrospira* as an Antifunal

According to an eighth aspect of the present invention, there is provided a composition for use as an antifungal, said composition comprising an effective amount of physiologically stressed *Arthrospira*.

According to a ninth aspect of the present invention, there is provided a method for preventing or treating a fungal infection or infestation of a subject, said method comprising the step of administering to the subject an effective amount of a composition comprising physiologically stressed *Arthrospira*.

Preferably, the method comprises the step of identifying a subject in need of such treatment or requiring such prevention.

There is also provided the use of physiologically stressed *Arthrospira* in the preparation of a medicament for the prevention or treatment of a fungal infection or infestation of a subject.

Physiologically stressed *Arthrospira* may be used to treat at least the following types of fungi: *Zygomycotina; Ascomycotina; Fungi Imperfecti; Malassezia; Microsporum; Trichophyton;* and *Epidermophyton*.

In a first embodiment, the subject is a human or an animal such as, mammal or vertebrate. In human subjects, the composition can be used to treat:
  tinea (e.g. athlete's foot, jock itch, ringworm, deep nail bed infection) which is caused chiefly by species of *Microsporum, Trichophyton, Candida and Epidermophyton;*
  thrush, which is caused by *Candida;*
  dandruff, which is caused by *Malassezia;*
  tropical mycetoma—a granular spreading growth in the skin, muscle tissue and lymph nodes—which is caused by *Madurella;*
  sporothricosis—a granular spreading growth in skin and lymph nodes—which is caused by *Sporothrix schenkii;* and
  histoplasmosis—a chronic pneumonia with spreading systemic infection—which is caused by *Histoplasma capsulatum.*

In animal subjects, the composition can be used to treat, for example, ring worm, hoof infections (*Candida, Malassezia*), dermatitis and folliculitis (*Microsporum, Trichophyton, Alternaria, Fusarium*). Topical fungal conditions in animals are usually caused by the same fungi as in humans.

In a second embodiment, the subject is an agricultural or horticultural product such as a plant, flower, fruit, vegetable, cereal, grain, pulse, mushroom spawn, pasture or lawn. The composition can be used to treat, for example, head blight and crown rot (*Fusarium*), facial eczema (*Pithomyces chartarum*), botrytis (*Botrytis cineria*), leaf spot (*Septoria, Alteria, Bipolaris*), powdery mildew (*Sphaerotheca macularis, Erysiphe, Sphaerotheca pannosa*), brown rot (*Monilinia fruiticola*) and leaf/stem rust (*Puccinia*).

In a third embodiment, the subject is soil, timber, building material or a building. The composition can be used, for instance, in or on buildings for the treatment of mould, and on building materials and power poles for the treatment of fungal wood rot.

Surprisingly, the present inventors have found that physiologically stressed *Arthrospira* interacts synergistically with monographed anti-fungal actives (fungi-static agents) to provide superior broad spectrum antifungal activity. The inventors have found that stressed *Arthrospira* can inhibit the growth of fungi, kill fungi and prevent regrowth of fungi.

According to a tenth aspect of the present invention, there is provided an antifungal composition comprising a synergistic combination of physiologically stressed *Arthrospira* and at least one fungi-static agent.

According to an eleventh aspect of the present invention, there is provided a method for preventing or treating a fungal infection or infestation of a subject, said method comprising the step of administering to the subject an effective amount of a composition comprising a synergistic combination of physiologically stressed *Arthrospira* and at least one fungi-static agent.

Preferably, the method comprises the step of identifying a subject in need of such treatment or requiring such prevention.

There is also provided the use of physiologically stressed *Arthrospira* in combination with at least one fungi-static agent in the preparation of a medicament for the prevention or treatment of a fungal infection or infestation of a subject.

Any suitable fungi-static agent (monographed active) can be used, such as terbinafine, bifonazole, clotrimazole, miconazole, econazole, ketoconazole or tolnaftate. Any suitable concentration of monographed active can be used and will depend on the intended use for the composition.

Use of Physiologically Stressed *Arthrospira* as an Antibacterial

Physiologically stressed *Arthrospira* has been found by the inventors to be an effective antibacterial against Gram-positive bacteria. The mode of antibacterial action is not clearly understood. It is possible that cell walls of Gram-positive bacteria are lysed or otherwise modified by one or more bioactives from *Arthrospira*. The cell walls contain peptidoglycan (comprising N-acetylglucosamine and N-acetylmuramic acid) and peptidoglycan may be digestible by one or more of the bioactives.

According to a twelfth aspect of the present invention, there is provided a composition for use as an antibacterial, said composition comprising an effective amount of physiologically stressed *Arthrospira*.

According to a thirteenth aspect of the present invention, there is provided a method for preventing or treating a bacterial infection or infestation of a subject, said method comprising the step of administering to the subject an effective amount of a composition comprising physiologically stressed *Arthrospira*.

Preferably, the method comprises the step of identifying a subject in need of such treatment or requiring such prevention.

There is also provided the use of physiologically stressed *Arthrospira* in the preparation of a medicament for the prevention or treatment of a bacterial infection or infestation of a subject.

Preferably, the bacteria is Gram-positive bacteria and may be, for example, *Bacilli, Clostridia, Staphylococci* or *Pneumococci*. The bacteria is preferably *Propionibacterium acne*, the causative agent of acne.

In a first embodiment, the subject is a human or an animal such as a mammal or vertebrate. In human subjects, the composition can be used to treat acne, dermatitis, ulcers or wounds caused by or infected with Gram-positive bacteria. The composition can be used to treat internal infections, such as those in the airways, in the mouth, in the digestive and in genitourinary tracts (e.g. strep throat, middle ear infections).

In a second embodiment, the subject is an agricultural or horticultural product such as a plant, flower, fruit, vegetable, cereal, grain, pulse or mushroom spawn.

In a third embodiment, the subject is, for example, soil, a man-made structure, or a waterway in which bacteria can grow.

Use of Physiologically Stressed *Arthrospira* as a Pesticide

According to a fourteenth aspect of the present invention, there is provided a composition for use as a pesticide, said composition comprising an effective amount of physiologically stressed *Arthrospira*.

According to a fifteenth aspect of the present invention, there is provided a method for suppressing or removing a pest, said method comprising administering or applying an effective amount of a composition comprising physiologically stressed *Arthrospira*.

The pesticide can be directed to pests such as crustacean and acari. The pesticide can be directed to insects such as flies (eg. *Simulidae*—black flies), wasps, mosquitoes and termites. The pesticide can be used to stop the transmission of parasites, such as those causing malaria, and other insects-borne diseases.

In a first embodiment, the composition can be formulated as an insect repellent or bait.

In a second embodiment, the composition can be applied to an agricultural or horticultural product such as a plant, flower, fruit, vegetable, cereal, grain, pulse or mushroom spawn.

In a third embodiment, the composition can be applied to, for example, soil, a man-made structure, a building, building material, a stream, a lake or wetlands.

Use of *Arthrospira* as a Therapeutic

When using physiologically stressed *Arthrospira* as a biocide and/or therapeutic on skin, the inventors have found that one or more other substituents of *Arthrospira* interact synergistically with the one or more bioactive agents to promote healing of the skin. These other substituents are likely to include: beta-carotene, which provides nourishment to the skin; phycocyanin, which is an anti-inflammatory; other proteins; and other nutrients, including vitamins, minerals, trace elements, anti-oxidants, essential oils and carbohydrates.

First, the stressed *Arthrospira* inhibits or kills the microbe—be it a fungus, bacteria or virus—and then other substituents of *Arthrospira* repair the damage caused by the microbe.

The present inventors have found that *Arthrospira* has therapeutic qualities even when not physiologically stressed, such as in the treatment of skin conditions and in skin repair.

According to a sixteenth aspect of the present invention, there is provided a composition for repairing or preventing a defect of the skin of a mammal, said composition comprising an effective amount of *Arthrospira*.

Preferably, the composition comprises physiologically stressed *Arthrospira*.

According to a seventeenth aspect of the present invention, there is provided a method of repairing or preventing a defect of the skin of a mammal, said method comprising the application of an effective amount of a composition comprising *Arthrospira*.

Preferably, the composition comprises physiologically stressed *Arthrospira*.

Preferably, the method comprises the step of identifying a mammal in need of such treatment or requiring such prevention.

There is also provided the use of *Arthrospira*, preferably physiologically stressed *Arthrospira*, in the preparation of a medicament for repairing or preventing a defect of the skin of a mammal.

The compositions according to the sixteenth and seventeenth aspects of the invention can have one or more ingredients or properties as described for the compositions according to the other aspects of the invention that have been defined.

The compositions according to the sixteenth and seventeenth aspects of the invention are preferably prepared by any of the methods described above.

The skin defect can be, for example, a pit, acne damage, rosacea, a reddened area, a crack, a burn, a blister, psoriasis, eczema, scaling, wrinkles, a papule, a stomatitis, a lesion, a pustule, a wound, cradle cap, diaper rash, an ulcer, a cold sore, shaving rash, chicken pox, dermatitis, cracked heels and elbows. The composition can be used to treat burns, insect and animal bites, and to remove inflammation of the skin. The composition can be used to reduce itchiness of the skin. The composition can be used to repair scar tissue, sun-damaged skin, and dry and scaly skin that has lost its elasticity.

Other aspects and embodiments of the invention will become apparent from the following detailed description thereof.

BRIEF DESCRIPTION OF THE FIGURES

FIG. 16 shows *T. mentagrophytes* inhibitory results using AMYCOT® in combination with a monographed active and various monographed actives;

FIG. 17 shows *C. albicans* inhibitory results using AMYCOT® in combination with a monographed active and various monographed actives;

FIG. 20 shows *T. mentagrophytes* inhibitory results using AMYCOT® in combination with a monographed active and various monographed actives;

FIG. 21 shows *C. albicans* inhibitory results using AMYCOT® in combination with a monographed active and various monographed actives;

BEST MODE AND OTHER MODES OF CARRYING OUT THE INVENTION

By way of illustration only, preferred embodiments of the present invention are described in detail, with reference to the following series of examples.

Example 1

Preparation of Physiologically Stressed *Arthrospira*

A culture of *Arthrospira maxima* (obtainable from Biovite Australia Pty Ltd) was stressed by nutrient diminution or partial desiccation. The *Arthrospira* was dewatered and dried to form an "unprocessed" powder. Dried *Arthrospira* was then explosively decompressed (potentiated) using the method described in New Zealand Patents No. 328013 and No. 328740. The *Arthrospira* was re-hydrated, decolourised, dried and milled to form a dry "premix powder". The premix powder was then dispersed in a suitable carrier (eg. commercially available aqueous British Pharmacopoeia cream or water). The premix powder is referred to as "AMYCOT® premix powder".

Example 2

Characterisation of Activity of Stressed *Arthrospira*

The results of respirometry suggest that physiologically stressed *Arthrospira* is capable of modifying or lysing substrates comprising chitin, chitosan and/or N-acetyl-D-glucosamine.

Chitin Substrate

Standard amounts of AMYCOT® premix powder and the unprocessed powder were separately reacted with four-unit polymer BHD chitin (Sigma, catalogue number C7170) in a Warburg Respirometer using standard techniques. Each composition was mixed together with chitin and the quantity of gas evolved was measured. The reaction was monitored for one-hour following equilibration for 30 minutes. The same composition, but pre-boiled in a water bath for five minutes, did not produce any gas which suggested that the activity could be enzymic and could be due to one or more types of denaturable proteins.

Figure 1:
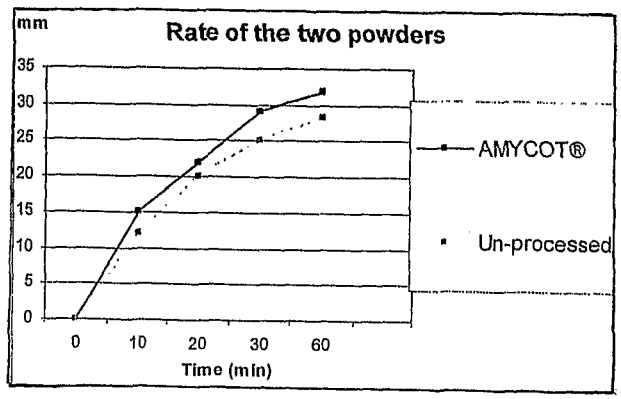
FIG. 1 shows activity of physiologically stressed *Arthrospira* (AMYCOT® and unprocessed powder) on chitin as assessed by respirometry.

The results are plotted in FIG. 1. The rate of activity (presumably enzymatic activity) of unprocessed powder was 694.9 ml/g cellular material/g substrate/hour. The rate of activity of AMYCOT® premix powder was 729.65 ml/g cellular material/g substrate/hour.

Figure 29:
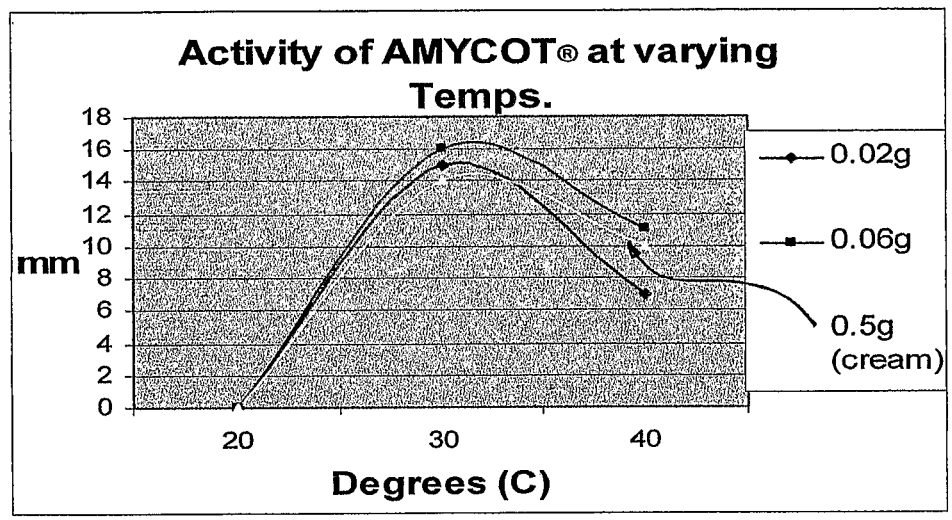
FIG. 29 shows activity of physiologically stressed *Arthrospira* (AMYCOT®) on chitin at different temperatures as assessed by respirometry.

Respirometry was also used to identify the optimum temperature for the activity. AMYCOT® premix powder (0.02 g and 0.06 g) was incubated with chitin (0.02 g) at 20° C., 30° C., 33° C. and 40° C. AMYCOT® premix powder in a cream based (0.05 g) was also incubated with chitin (0.02 g) at those temperatures. The results are plotted in FIG. 29. The optimum temperature for the activity in each case was determined to be 33° C.

Figure 30:
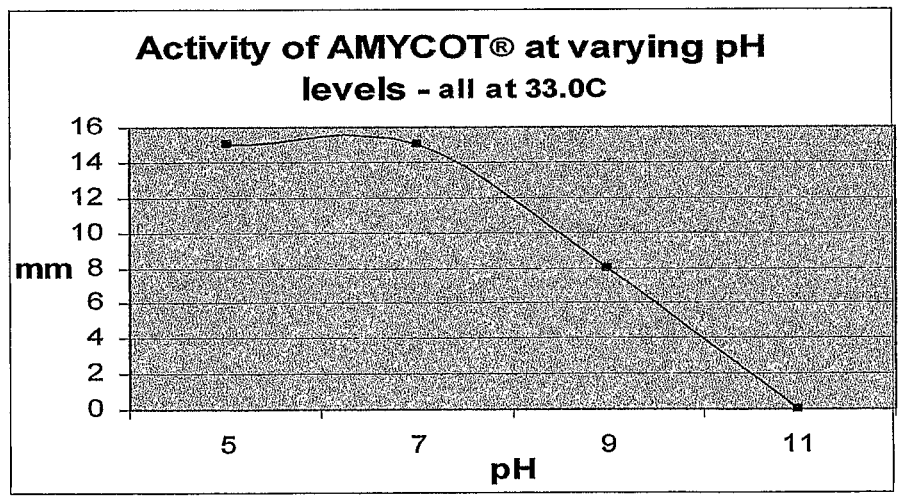
FIG. 30 shows activity of physiologically stressed *Arthrospira* (AMYCOT®) on chitin at various pH conditions as assessed by respirometry.

Respirometry was also used to identify the optimum pH for the activity. AMYCOT® premix powder (0.02 g) was suspended in buffers of varying pH (60-70% ethanol, 30-40% water, 0-0.05% phenolphthalein, 0-0.03% bromothymol blue, 0-0.02% methyl red, sodium salt, 0-0.01% sodium hydroxide and 0-0.01% methyl orange, sodium salt at pH 5, 7, 9 and 11) and was incubated with chitin (0.02 g) at 33° C. The results are plotted in FIG. 30. The optimum pH for activity was determined to be 6.

These results suggest that the bioactive agent or agents should have activity when topically applied to skin as skin has a similar temperature and pH.

N-acetyl-D-glucosamine and Chitosan Substrates

AMYCOT® premix powder (0.02 g) was separately incubated with N-acetyl-D-glucosamine (0.02 g, Sigma catalogue number A8625-5G) and chitosan (0.02 g, Sigma catalogue number C3646) substrates in a Warburg Respirometer at 33° C. Each reaction was monitored for one-hour following equilibration for 30 minutes.

The results for AMYCOT® plus N-acetyl-D-glucosamine are presented in the table below.

TABLE 1

| AMYCOT ® + N-acetyl-D-glucosamine | | | |
|---|---|---|---|
| Time (min) | mm of gas | mm of gas | mm of gas |
| 0 | 0 | 0 | 0 |
| 5 | 9 | 6 | 7 |
| 10 | 12 | 9 | 11 |
| 30 | 12 | 10 | 11 |
| 60 | 12 | 10 | 11 |

The results for AMYCOT® plus chitosan are presented in the table below.

TABLE 2

| AMYCOT ® + Chitosan | | | |
|---|---|---|---|
| Time | mm of gas | mm of gas | mm of gas |
| 0 | 0 | 0 | 0 |
| 5 | 12 | 10 | 10 |
| 10 | 14 | 12 | 14 |
| 30 | 17 | 13 | 15 |
| 60 | 17 | 14 | 16 |

For comparison, results for AMYCOT® (0.02 g) plus chitin (0.02 g), incubated at 33° C., are presented in the table below.

TABLE 3

| AMYCOT ® + Chitin | | | |
|---|---|---|---|
| Time | mm of gas | mm of gas | mm of gas |
| 0 | 0 | 0 | 0 |
| 5 | 12 | 10 | 15 |
| 10 | 18 | 18 | 20 |
| 30 | 19 | 18 | 21 |
| 60 | 19 | 19 | 21 |

These results suggest that physiologically stressed *Arthrospira* has one or more bioactive agents that lyse or modify chitin, chitosan and/or N-acetyl-D-glucosamine, or possibly another type of polymer having N-acetyl-D-glucosamine as a polymer subunit. The bioactive agent could be, for instance, a chitinase, chitosanase or chitin deacetylase.

Example 3

Antifungal and Antibacterial Activity of Stressed *Arthrospira*

The biocidal activity of AMYCOT® premix powder was tested in vitro on live fungi and Gram-positive bacteria.

Live cultures of target pathogens were sourced from the American Type Culture Collection (ATCC), the Australian Collection of Microorganisms (ACM) and Sullivan Niccolaides. The cultures that were tested are shown in Table 4.

TABLE 4

| Pathogen | ATCC No. | ACM No. | Isolates |
|---|---|---|---|
| Trichophyton mentagrophytes | 4808, 9533 | 5068 | |
| Candida albicans | 753 | 4574 | |
| Trichophyton rubrum | | | SN01 (Sullivan Niccolaides) |
| Epidermophyton floccosum | | | SN02 (Sullivan Niccolaides) |
| Propionibacterium acne | 25746 | 5109 | |

A uniform lawn of each pathogen was grown on a dish containing Potato Dextrose Agar (PDA) medium. After 3-4 days of incubation, four wells were cut in the PDA medium with a sterile 8 mm diameter cork borer. Measured amounts of AMYCOT® premix powder and control creams/powders were placed in each well. The dishes were cultured at conditions appropriate for the respective pathogen and the dishes were inspected daily.

After 2-4 days two concentric zones around the well were evident:

1. A smaller transparent circular "clearance" zone around a well. This is an area where fungi have been destroyed, leaving only residual dry cytoplasmic matter (as seen by light and electron microscopy).

2. A larger semitransparent "affected" zone extending from the perimeter of the clearance zone. The affected zone is recognised by the lesser height of the lawn, its lesser density and greater transparency compared with unaffected lawn. This is an area where fungi cell walls have been largely destroyed, but that some are still present, often as rounded cytoplasmic spheres (as seen by light and electron microscopy).

Measurement of the zones is taken from the outside perimeter of the well to the outside perimeter of the zone in each case. This measurement is referred to as the zonal distance (ZD). The radius of the zones is a non-linear measure of the efficacy of the biocidal agent/s against the pathogen in vitro.

The in vitro control results are shown in Table 5.

TABLE 5

| | Pathogen | Result | Size of clearance zone (ZD) (mm) | Size of affected zone (mm) |
|---|---|---|---|---|
| ACM No. | | | | |
| 5068 | Trichophyton mentagrophytes | Clearance | 6 | 10 |
| 4574 | Candida albicans | Clearance | 6.5 | — |
| 5109 | Propionibacterium acne (cultured anaerobically) | No clearance | — | — |
| ATCC No. | | | | |
| 4808 | Trichophyton mentagrophytes | Clearance | 5 | 8 |
| 9533 | Trichophyton mentagrophytes | Clearance | 6 | 10 |
| 753 | Candida albicans | Clearance | 6.5 | — |
| 25746 | Propionibacterium acne (cultured anaerobically) | No clearance | — | — |
| Isolate No. | | | | |
| SN01 | Trichophyton rubrum | Clearance | 6 | — |
| SN02 | Epidermophyton floccosum | Clearance | 5 | 8 |
| 301 | Tinea pedis-isolate | Clearance | 6 | 10 |
| 307 | Jockey itch-isolate | Clearance | 6 | 10 |

Figure 2:
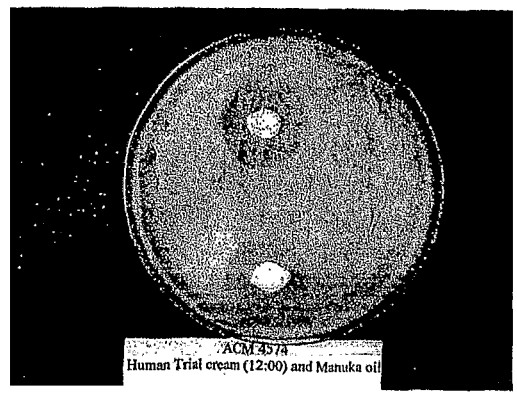
FIG. 2 shows antifungal activity of AMYCOT® on *C. albicans*.

FIG. 2 shows clearance of Canada albicans (ACM 4574) using AMYCOT®, which is evidence of the efficacy of one or more biocidal agents against the condition thrush. AMYCOT® premix powder is at the 6 o'clock position and a "human trial cream" having 12.5% w/w AMYCOT® in an aqueous cream is at the 12 o'clock position (ZD of 9 mm).

In the case of the anaerobic acne-causing bacteria *Propionibacterium acne*, no clearance was obtained when tested under anaerobic conditions. An explanation for this is provided in Example 4.

Example 4

Antibacterial Activity of Stressed *Arthrospira* on *Propionibacterium acne* Respirometry showed that AMYCOT® has antibacterial activity against *P. acne*.

AMYCOT® premix powder (0.02 g) and 5 g "human trial cream" comprising 12.5% w/w AMYCOT® were separately reacted with a broth of the anaerobic acne-causing organism *P. acne* (ACM No. 5109) in a Warburg Respirometer in the presence or absence of oxygen. The results were compared with those of a control comprising *P. acne* broth devoid of AMYCOT®. In the absence of oxygen, no gas was liberated. In the presence of oxygen, gas was liberated and each composition had antibacterial activity.

Figure 3:
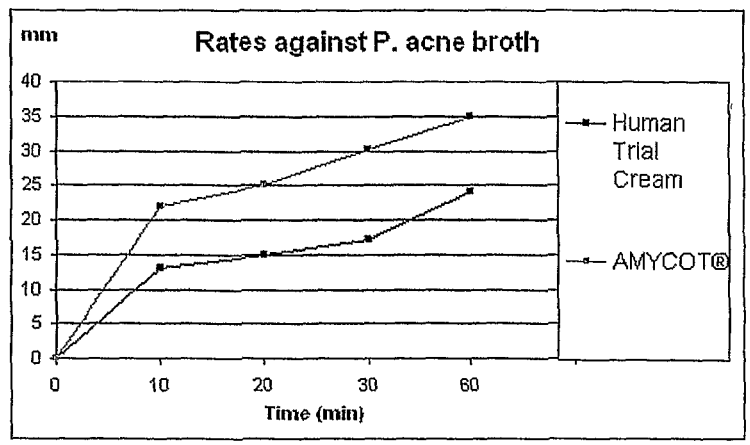
FIG. 3 shows antibacterial activity of AMYCOT® on *P. acne* as assessed by respirometry.

The results for AMYCOT® and human trial cream in the presence of oxygen are plotted in FIG. 3. The (presumably enzymatic) rate of AMYCOT® premix powder was 626.00 ml/g cellular material/g substrate/hour. The rate of human trial cream was 12.00 ml/g cellular material/g substrate/hour.

The results showed that in order for the composition to work as an antibacterial on *P. acne* in vivo, the presence of oxygen is required. Therefore, at least one of the biocidal agents may be an oxidase.

The inventors suspect that one or more of the biocidal agents against fungi may lyse or modify the cellular wall of fungi. Such an agent may be a chitinase, chitosanase or chitin deacetylase.

Although *P. acne* and other Gram-positive bacteria are not believed to have chitin or chitosan in their cellular walls, it is suspected that one or more biocidal agents lyse or modify N-acetyl-D-glucosamine/peptidoglycans in the bacterial cell wall.

Example 5

Different Commercial Sources of *Arthrospira* have Antifungal Activity

Commercial preparations of dried *Arthrospira* (powders, tablets and capsules) were sourced from different suppliers in different jurisdictions and tested for antifungal activity. The powders are typically prepared by harvesting *Arthrospira*, washing the harvested *Arthrospira*, and drying the washed *Arthrospira*. Some suppliers mill the *Arthrospira* whilst wet. Preparation does not entail the step of specifically stressing *Arthrospira* post-harvest such that the *Arthrospira* enter the anabiotic state. In fact, as mentioned before, commercial growers of *Arthrospira* tend to minimise stressing of the organism as much as possible as the thick mucoid coating tends to clog machinery for processing the organism.

*Arthrospira* (Spirulina) powders were obtained from the following suppliers:
1. China *Spirulina*—Jiangsu Cibainian Nutrition Food Co., Ltd. China
2. Febico—Far East Biotech Co. Ltd. Taiwan
3. Life Stream/Earthrise—DIC. California USA
4. Pacifica—Cyanotech. Hawaii USA
5. Siam Algae Co.—DIC. Thailand
6. Spirin—Yunnan Spirin Co. Ltd. China
7. Synergy—DIC. China Each powder was mixed in an aqueous cream using 12.5% w/w concentration. Each cream was then decolourised. A uniform lawn of *T. rubrum* was grown on PDA medium in a dish. After 3-4 days of incubation, wells were cut in the PDA medium with a sterile cork borer. Measured amounts of each cream were placed in a respective well, the dishes were then incubated for 2-4 days.

Figure 4:
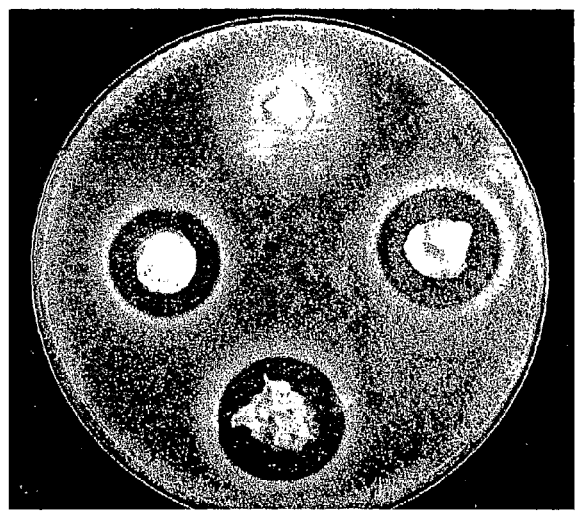
FIG. 4 shows the antifungal activity of different commercial preparations of *Arthrospira* (Spirulina) on *T. rubrum*.

FIG. 4 shows the antifungal activities of 12.5% w/w Siam Algae Co. (3 o'clock position), 12.5% w/w Life Stream (6 o'clock position), and 12.5% w/w China *Spirulina* (9 o'clock position).

The results showed that all commercial powders tested had some antifungal activity. Respirometry confirmed that all commercial powders tested also had activity (presumably enzymatic) when incubated with chitin (results not shown).

Figure 5:
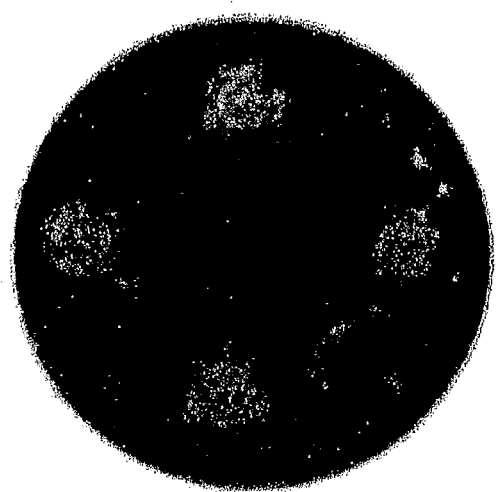
FIG. 5 shows antifungal activity of a commercial preparation (Life Stream) of *Arthrospira* on *A. niger*.

One powder (Life Stream) was randomly selected for blending with an over-the-counter aqueous cream at a concentration of 12.5% w/w without further processing and tested for antifungal activity against *Aspergillus niger*. The cream produced a clearance of 4 mm, as seen in FIG. 5 at the 12, 3, 6 and 9 o'clock positions. This indicated that possibly all commercial preparations of dried *Arthrospira* were likely to have some level of antifungal activity, without requiring an additional stressing step or further processing step such as filament disruption.

Example 6

Activity of Stressed *Arthrospira* Against Fungal Diseases of Mammals

The antifungal activity of AMYCOT® was tested in vitro against different fungal diseases of mammals. The following pathogens were sourced from the Department of Primary Industries, Department of Agriculture, ACM and nurseries:
*Candida albicans*
*Microsporum canis*
*Trichophyton mentagrophytes*
*Trichophyton rubrum*
*Epidermophyton floccosum*
*Fusarium graminearum*
*Alternaria* sp.
*Malassezia furfur*

A uniform lawn of each pathogen was grown on PDA medium. After 1-2 days of incubation, wells were cut in the PDA medium with a sterile 8 mm diameter cork borer. Measured amounts of AMYCOT® were placed in each well. The plates were cultured at an appropriate temperature depending on the pathogen. The welled plates were inspected daily. The clearance was measured after 2-3 days. Measurement of the zone is taken from the perimeter of the well to the outside perimeter of the zone.

This zone was void of live fungal cells proving efficacy of AMYCOT® against the target pathogens.

12.5% w/w AMYCOT® cream produced a clearance of 8 mm of the pathogen *T. rubrum*. *T. rubrum* is a causal agent of hoof infections and ring worm.

12.5% w/w AMYCOT® cream produced a clearance of 15 mm of the pathogen *T. mentagrophytes*. *T. mentagrophytes* is a causal agent of hoof infections and ring worm.

Figure 6:
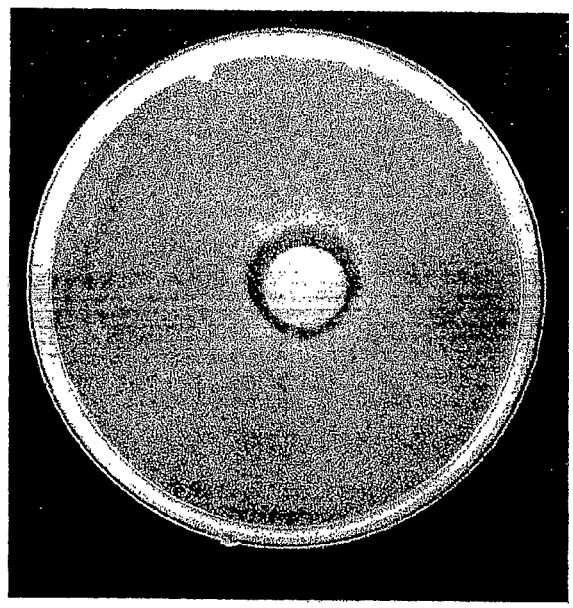
FIG. 6 shows antifungal activity of AMYCOT® on *M. canis*.

FIG. 6 shows a well of 12.5% w/w AMYCOT® cream produced a clearance of 3 mm of the pathogen, *M. canis*. *M. canis* is a causal agent of hoof infections and ring worm.

12.5% w/w AMYCOT® cream produced a clearance of 3 mm of the pathogen *E. floccosum*. *E. floccosum* is a casual agent of hoof infections and ring worm.

12.5% w/w AMYCOT® cream produced a clearance of 4.5 mm of the pathogen *C. albicans*. *C. albicans* is a causal agent of ring worm and dermatitis.

Figure 7:
FIG. 7 shows antifungal activity of AMYCOT® on *F. graminearum*.

FIG. 7 shows a well of 12.5% w/w AMYCOT® cream produced a clearance of 12 mm of the pathogen *F. graminearum*. *F. graminearum* is a causal agent of hoof infections.

Figure 8:
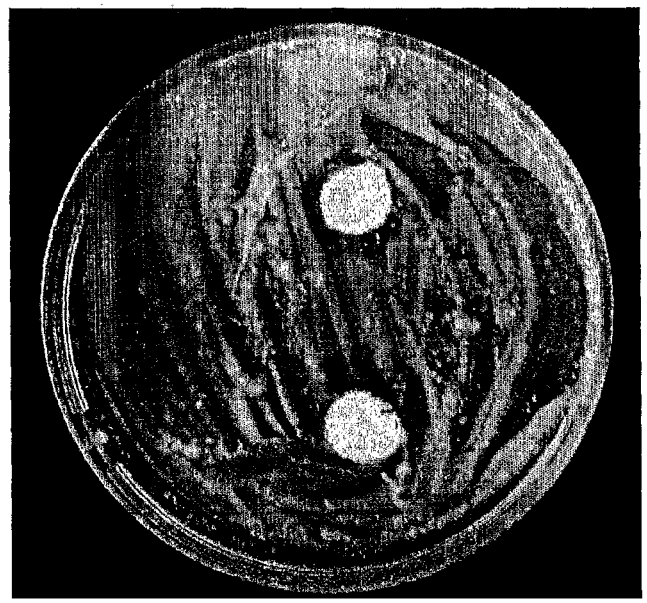
FIG. 8 shows antifungal activity of AMYCOT® on *M. furfur*.

FIG. 8 shows that wells of 12.5% w/w AMYCOT® cream produced clearances of *M. furfur*. *M. furfur* is a causal agent of dandruff.

Figure 9B:
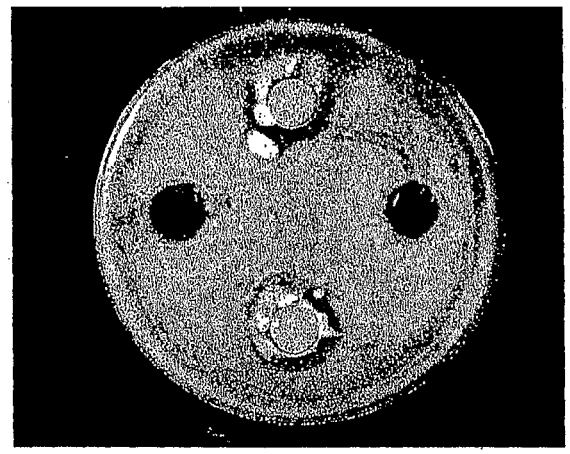
FIG. 9*b* shows antifungal activity of shampoo AMYCOT® on *C. albicans*.
Figure 9A:
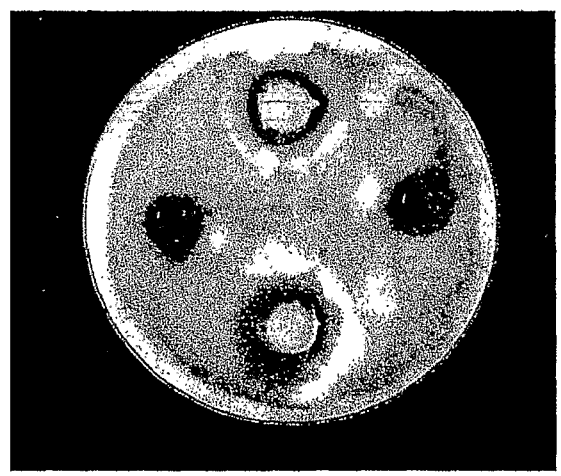
FIG. 9*a* shows antifungal activity of shampoo AMYCOT® on *T. rubrum*.

FIG. 9a shows a well of 5% w/w AMYCOT® shampoo produced a clearance of 3 mm of the pathogen *T. rubrum*.

FIG. 9b shows a well of 5% w/w AMYCOT® shampoo produced a clearance of 4 mm of the pathogen *C. albicans*.

Example 7

Activity of Stressed *Arthrospira* Against Fungal Diseases of Plants

The antifungal activity of AMYCOT® was tested in vitro against different fungal diseases of plants. The following pathogens were sourced from the Department of Primary Industries, Department of Agriculture, ACM and nurseries:
*Fusarium graminearum*
*Pithomyces Chartarum*
*Botrytis cinerea*
*Alternaria* sp.

A uniform lawn of each pathogen was grown on PDA medium. After 1-2 days of incubation, wells were cut in the PDA medium with a sterile 8 mm diameter cork borer. Measured amounts of AMYCOT® were placed in each well. The plates were cultured at an appropriate temperature depending on the pathogen. The welled plates were inspected daily.

The clearance was measured after 2-3 days. Measurement of the zone was taken from the perimeter of the well to the outside perimeter of the zone.

The zone was void of live fungal cells proving efficacy of AMYCOT® against the target pathogens.

12.5% w/w AMYCOT® cream produced a clearance of 13 mm of the pathogen *F. graminearum*. *F. graminearum* is a causal agent of head blight and crown rot in small grain.

Figure 10:
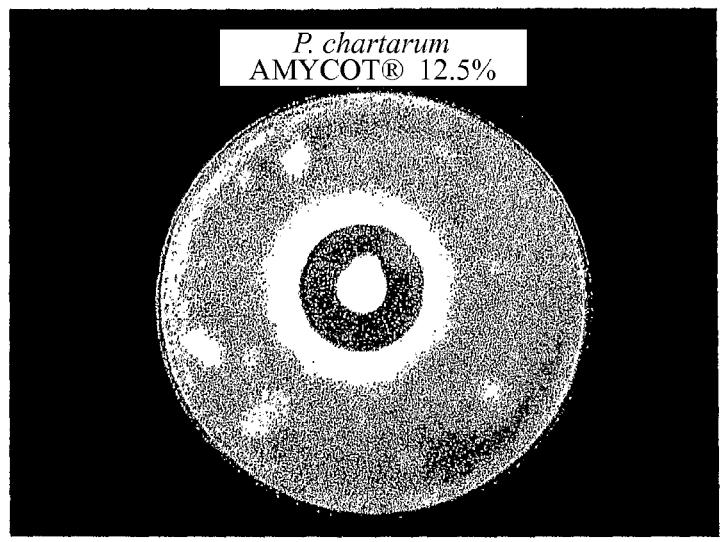
FIG. 10 shows antifungal activity of AMYCOT® on *P. chartarum*.

FIG. 10 shows a well of 12.5% w/w AMYCOT® cream produced a clearance of 10 mm of the pathogen *P. chartarum*. *P. chartarum* is a causal agent of facial eczema in sheep cattle.

12.5% w/w AMYCOT® cream produced a clearance of 8 mm of the pathogen *B. cinerea*. *B. cinerea* is a causal agent of botrytis in fruit.

12.5% w/w AMYCOT® cream produced a clearance of 9 mm of the pathogen *Alternaria* sp, the casual agent of leaf spot in fruit.

Example 8

Testing of AMYCOT® as a Spray on Plant Fungal Pathogens

AMYCOT® in the form of an antifungal spray was tested in vitro against a common plant pathogen, *Botrytis cinerea*. 5% w/w AMYCOT® powder was hydrated with water, but was only sparingly soluble.

Figure 11:
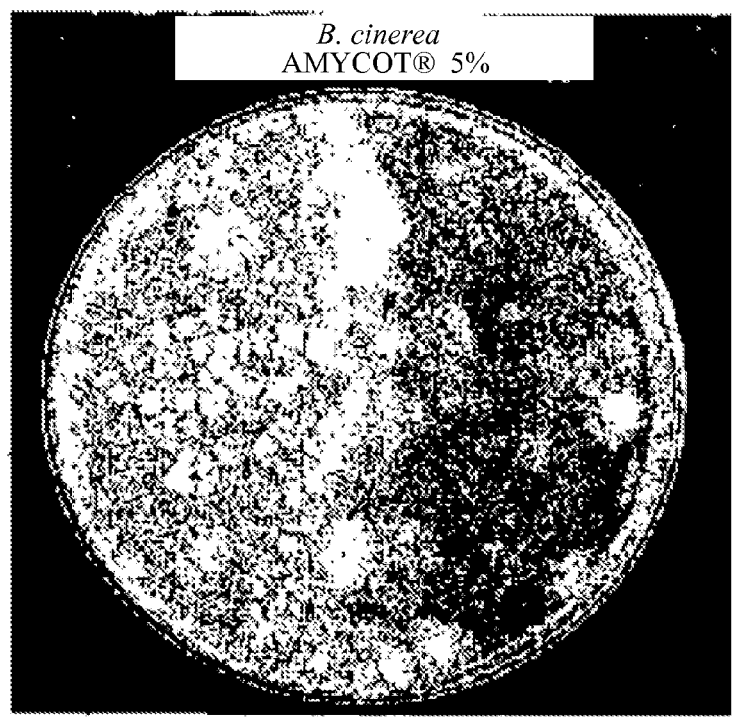
FIG. 11 shows antifungal activity of AMYCOT® on *B. cinerea*.
Figure 15:
FIG. 15 shows *C. albicans* inhibitory results using a monographed active.
Figure 12:
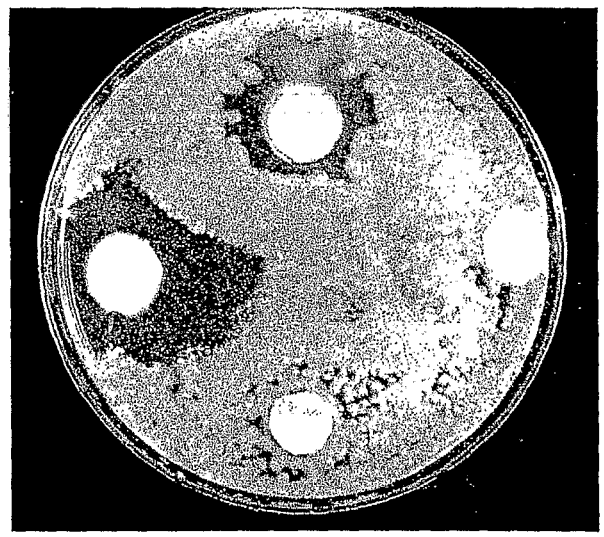
FIG. 12 shows *T. rubrum* inhibitory results using AMYCOT® and various monographed anti-fungal actives.
Figure 13:
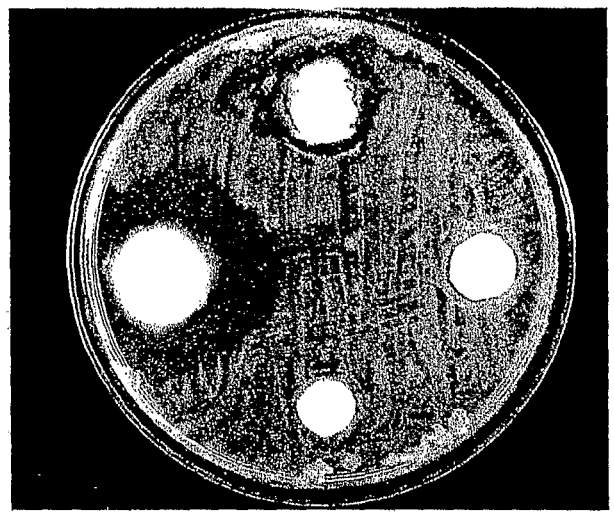
FIG. 13 shows *T. mentagrophytes* inhibitory results using AMYCOT® and various monographed actives.
Figure 14:
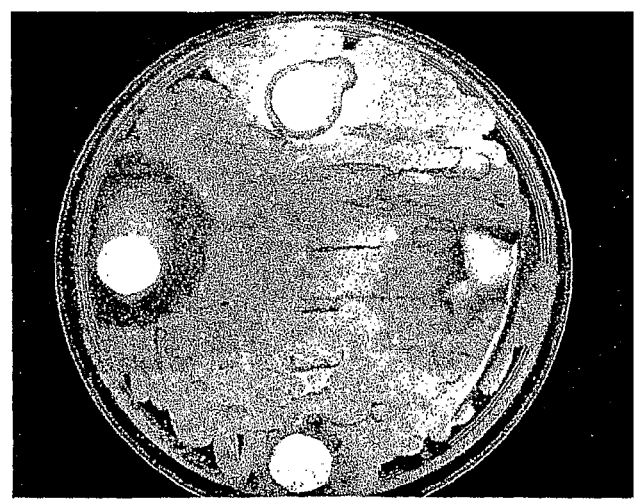
FIG. 14 shows *C. albicans* inhibitory results using AMYCOT® and various monographed actives.
Figure 18:
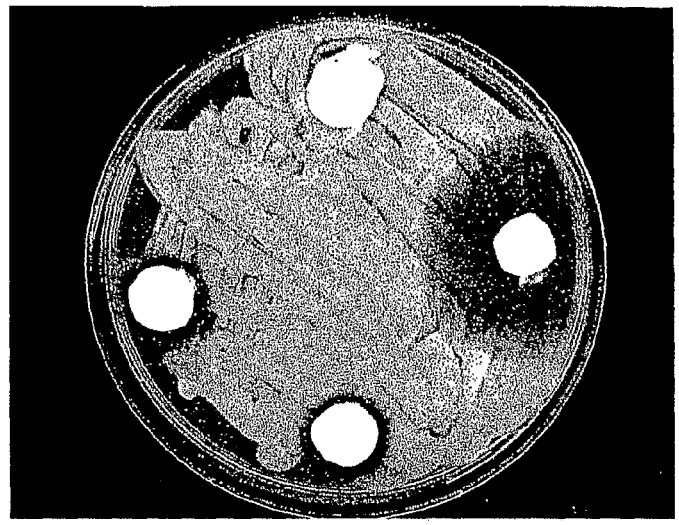
FIG. 18 shows *T. mentagrophytes* inhibitory results using AMYCOT® in combination with monographed actives.
Figure 19:
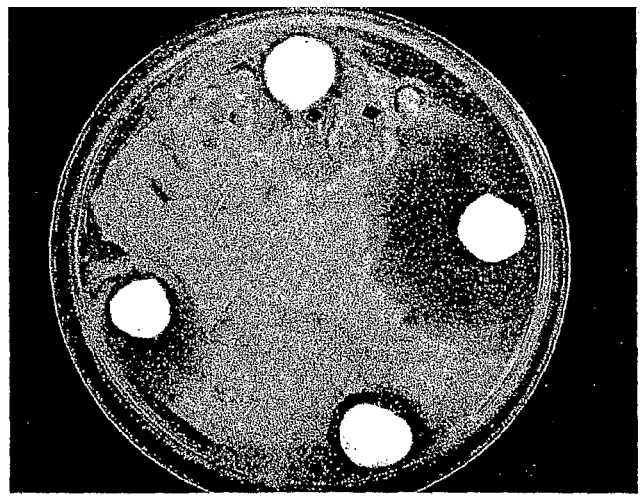
FIG. 19 shows *T. mentagrophytes* inhibitory results using AMYCOT® in combination with monographed actives.
Figure 22:
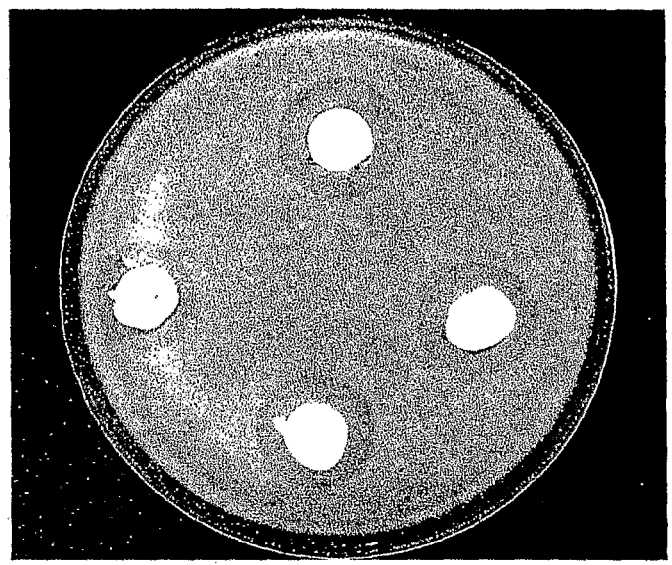
FIG. 22 shows *T. mentagrophytes* fungicidal results using AMYCOT® in combination with monographed actives.
Figure 23:
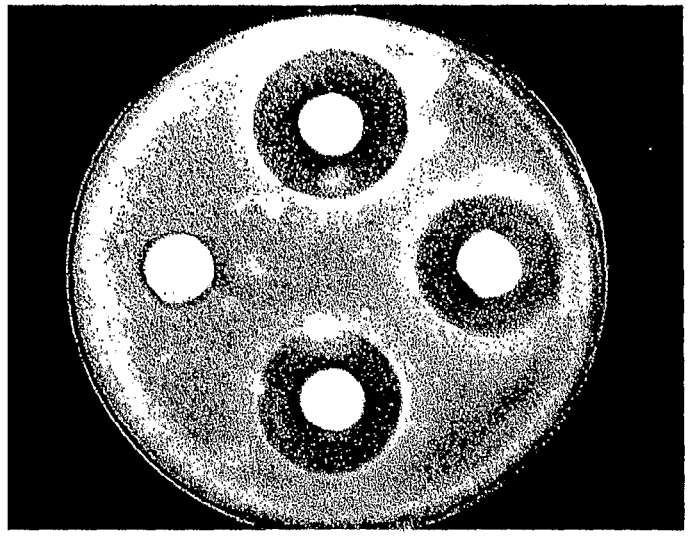
FIG. 23 shows *T. rubrum* fungicidal results using AMYCOT® in combination with monographed actives.
Figure 24:
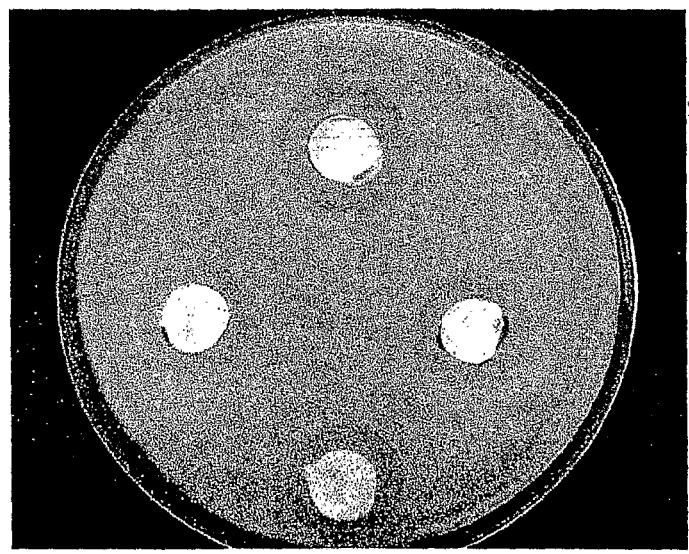
FIG. 24 shows *T. mentagrophytes* fungicidal results using AMYCOT® in combination with monographed actives.
Figure 25:
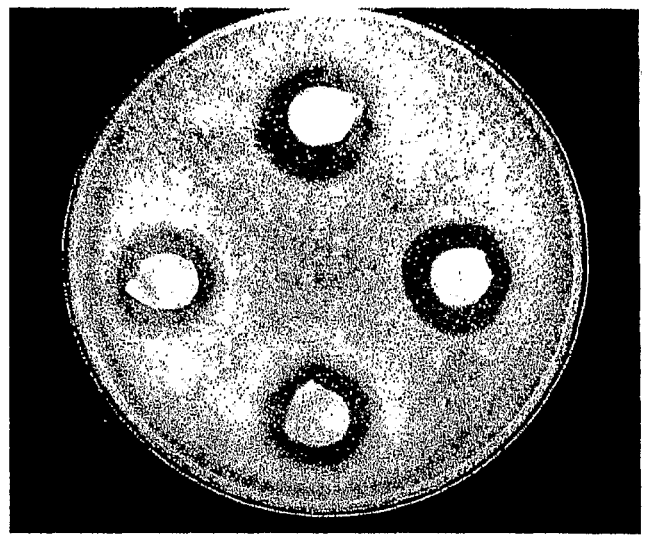
FIG. 25 shows *T. mentagrophytes* fungicidal results using AMYCOT® in combination with monographed actives.
Figure 26:
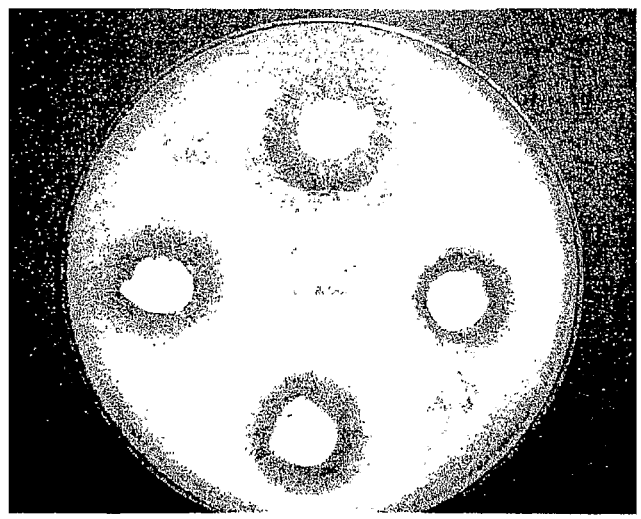
FIG. 26 shows *T. mentagrophytes* fungicidal results using AMYCOT® in combination with monographed actives.
Figure 27:
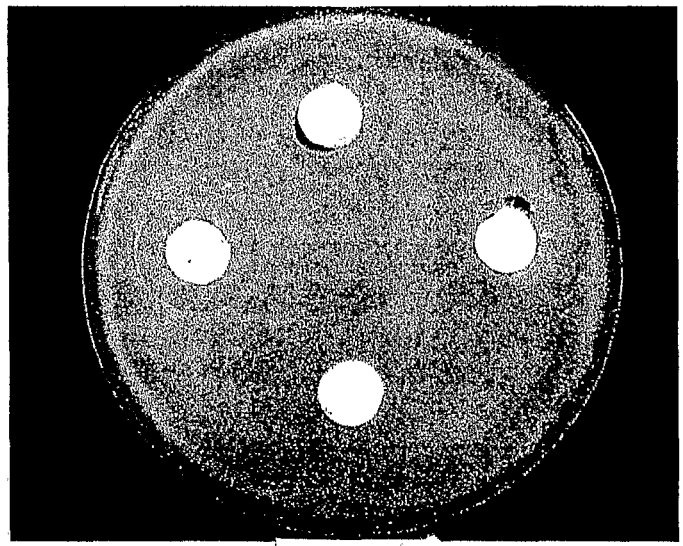
FIG. 27 shows *C. albicans* fungicidal results using AMYCOT® in combination with a monographed active and various monographed actives.

A uniform lawn of *B. cinerea* was grown on PDA medium in a dish. The right-hand side of the dish was then sprayed with the spray and allowed to sit at room temperature for 24 hours. The left-hand side of the dish was not sprayed. FIG. 11 shows that the sprayed side of the dish had dead fungi. The spray was effective in eliminating botrytis and inhibiting further sporulation.

Example 9

In Vitro Antimicrobial Tests with Stressed *Arthrospira* and Monographed Actives The antifungal and antibacterial activities of various over-the-counter fungal and antibacterial creams (including Lamisil™, Dakta Gold™, Canesten™, Tinaderm™, Daktarin™, Tripod Labs™, Resolve Tinea™, Resolve Balm™, Resolve Plus™, Clearasil™, Benzac W™) and AMYCOT® were tested in this and other examples.

In this example, the antifungal and antibacterial activities of various over-the-counter creams and AMYCOT® were tested by an independent laboratory (ConMac Laboratory Services) against the target pathogens *Trichophyton mentagrophytes, Epidermophyton floccosum, Trichophyton rubrum* and *Propionibacterium acne*.

The results are shown in Table 6.

The results show that only AMYCOT® was active against each pathogen. The only

TABLE 6

| Target Pathogen | Test Cream | Clearance Day 1 | Clearance Day 2 | Clearance Day 3 |
|---|---|---|---|---|
| *Trichophyton mentagrophytes* | 1) Control | Nil detected | Nil detected | Nil detected |
| | 2) Amycot ® | 0.5-1 mm not clear, round | 4 mm not clear, round | 1-2 mm clear, round 3-4 mm not clear, round |
| | 3) Lamisil | Nil detected | Nil detected | Nil detected |
| | 4) Dakta Gold | Nil detected | Nil detected | Nil detected |
| *Epidermophyton floccosum* | 1) Control | Nil detected | Nil detected | Nil detected |
| | 2) Amycot ® | 1 mm clear, round | 2.5 mm clear, round | 2.5 mm clear, round 5 mm not clear, round |
| | 3) Canesten | Nil detected | Nil detected | Nil detected |
| | 4) Lamisil | Nil detected | Nil detected | Nil detected |
| *Trichophyton rubrum* | 1) Control | Nil detected | Nil detected | Nil detected |
| | 2) Amycot ® | 1 mm clear, | 5.5 mm clear, | 5.5 mm clear, |

TABLE 6-continued

| Target Pathogen | Test Cream | Clearance Day 1 | Clearance Day 2 | Clearance Day 3 |
|---|---|---|---|---|
| | | round | round | round 4 mm not clear, round |
| | 3) Tinaderm | Nil detected | Nil detected | Nil detected |
| | 4) Lamisil | Nil detected | 1 mm clear, irregular | 1.5 mm clear, irregular |
| Propionibacterium acnes | 1) Control | Nil detected | Nil detected | Nil detected |
| | 2) Amycot ® | Nil detected | Nil detected | Nil detected |
| | 3) Clearasil | Nil detected | Nil detected | Nil detected |
| | 4) Benzac W | Nil detected | Nil detected | Nil detected | other instance of a cream showing activity was Lamisil™ against *T. rubrum*.

Example 10

In Vitro Tests with Monographed Actives and Combinations with AMYCOT®

Antifungals such as miconazole, tolnaftate, bifonazole and clotrimazole work by inhibiting specific protein production, preventing normal functions such as reproduction. The antifungal terbinafine works by preventing the formation of vital sterols.

The first aim of these in vitro tests was to determine the efficacies of various over-the-counter creams or their actives as fungal inhibitors and to compare the efficacy of AMYCOT®. The second aim was to determine the efficacy of AMYCOT® in combination with one or more of the over-the-counter creams or their actives as fungal inhibitors.

Sabouraud's liquid medium was inoculated with the chosen pathogen. The broths were then incubated for one week at 28° C. A sterile swab was dipped into a broth of the pathogen, and a PDA medium plate was inoculated by streaking the plate at right angles, insuring that the plate had an even lawn.

Monographed actives not already in a cream base were mixed with a respective cream base. A select cream was placed onto a 10 mm diameter filter paper disc and the disc was placed onto a newly inoculated plate. Up to four different discs were placed on a plate. The plate was then incubated for 24-48 hours at the appropriate temperature depending on the pathogen. Photos were then taken at the completion of the 24-48 hours.

The inhibitory test results are shown in FIGS. 12-21 and in Tables 7-16 below.

TABLE 7

Inhibitory Test (FIG. 12) Pathogen: *Trichophyton rubrum*

| Position | Agent | Size of Clearance (mm) |
|---|---|---|
| 12:00 | AMYCOT ® 12.5% cream | 8 |
| 3:00 | Tinaderm (tolnaftate 2%) | 0 |
| 6:00 | Placebo | 0 |
| 9:00 | Daktarin (miconazole 2%) | 15 |

TABLE 8

Inhibitory Test (FIG. 13) Pathogen: *Trichophyton mentagrophytes*

| Position | Agent | Size of Clearance (mm) |
|---|---|---|
| 12:00 | AMYCOT ® 12.5% cream | 4 |
| 3:00 | Tinaderm (tolnaftate 2%) | 1 |

TABLE 8-continued

Inhibitory Test (FIG. 13) Pathogen: *Trichophyton mentagrophytes*

| Position | Agent | Size of Clearance (mm) |
|---|---|---|
| 6:00 | Placebo | 0 |
| 9:00 | Daktarin (miconazole 2%) | 11 |

TABLE 9

Inhibitory Test (FIG. 14) Pathogen: *Candida albicans*

| Position | Agent | Size of Clearance (mm) |
|---|---|---|
| 12:00 | AMYCOT ® 12.5% cream | 2 |
| 3:00 | Tinaderm (tolnaftate 2%) | 3 |
| 6:00 | Placebo | 0 |
| 9:00 | Daktarin (miconazole 2%) | 15 |

TABLE 10

Inhibitory Test (FIG. 15) Pathogen: *Candida albicans*

| Agent | Size of Clearance (mm) |
|---|---|
| Tripod Labs (clotrimazole 1% + tea tree oil) | 10 |

TABLE 11

Inhibitory Test (FIG. 16) Pathogen: *Trichophyton mentagrophytes*

| Position | Agent | Size of Clearance (mm) |
|---|---|---|
| 12:00 | 50% AMYCOT ® 12.5% cream + 50% Daktarin (miconazole 2%) | 10 |
| 3:00 | Resolve Tinea (miconazole 2%) | 10 |
| 6:00 | Resolve Balm (miconazole 2%) | 7 |
| 9:00 | Resolve Plus (miconazole 2%) | 11 |

TABLE 12

Inhibitory Test (FIG. 17) Pathogen: *Candida albicans*

| Position | Agent | Size of Clearance (mm) |
|---|---|---|
| 12:00 | AMYCOT ® + Daktarin | 10 |
| 3:00 | Resolve Tinea (miconazole 2%) | 6 |
| 6:00 | Resolve Balm (miconazole 2%) | 7 |
| 9:00 | Resolve Plus (miconazole 2%) | 11 |

TABLE 13

Inhibitory Test (FIG. 18)
Pathogen: *Trichophyton mentagrophytes*

| Position | Agent | Size of Clearance (mm) |
|---|---|---|
| 12:00 | AMYCOT ® 12.5% cream | 1 |
| 3:00 | AMYCOT 12% + clotrimazole 10% | 13 |
| 6:00 | AMYCOT 12% + terbinafine 1% | 1 |
| 9:00 | AMYCOT 12% + tolnaftate 10% | |

TABLE 14

Inhibitory Test (FIG. 19)
Pathogen: *Trichophyton mentagrophytes*

| Position | Agent | Size of Clearance (mm) |
|---|---|---|
| 12:00 | AMYCOT ® 12.5% cream | 1 |
| 3:00 | AMYCOT 12% + clotrimazole 10% | 11 |
| 6:00 | AMYCOT 12% + terbinafine 1% | 2 |
| 9:00 | AMYCOT 12% + tolnaftate 10% | 4 |

TABLE 15

Inhibitory Test (FIG. 20)
Pathogen: *Trichophyton mentagrophytes*

| Position | Agent | Size of Clearance (mm) |
|---|---|---|
| 12:00 | AMYCOT ® 12.5% cream + miconazole 2% | 11 |
| 3:00 | Placebo | 0 |
| 6:00 | Resolve Balm (miconazole 2%) | 7 |
| 9:00 | Resolve Plus (miconazole 2%) | 7 |

TABLE 16

Inhibitory Test (FIG. 21)
Pathogen: *Candida albicans*

| Position | Agent | Size of Clearance (mm) |
|---|---|---|
| 12:00 | 50% AMYCOT ® 12.5% cream + 50% Daktarin (miconazole 2%) | 14 |
| 3:00 | 1% clotrimazole | 4 |
| 6:00 | 10% tolnaftate | 0 |
| 9:00 | 2% miconazole | 9 |

The monographed actives in FIG. 21 are in an aqueous cream base as opposed to a spirit base which is normally used.

In the in vitro tests miconazole and clotrimazole were seen as being the most effective inhibitors of pathological fungi, (see FIGS. 12-21). FIGS. 16 and 17 and Tables 11 and 12 establish that miconazole is an effective fungal inhibitor. AMYCOT® also acts as an inhibitor, but is only approximately 40% as effective as clotrimazole and miconazole (see FIGS. 12-14). FIGS. 18-21 and Tables 13-16 suggest that the combinations of AMYCOT® plus miconazole and AMYCOT® plus clotrimazole are the most effective fungal inhibitors in vitro when compared to terbinafine and tolnaftate.

The third aim of these in vitro tests was to determine the efficacies of various over-the-counter creams or their actives as fungicides and to compare the efficacy of AMYCOT®. The fourth aim was to determine the efficacy of AMYCOT® in combination with monographed actives.

The fungicidal test involved growing a lawn of the pathogen on PDA medium plates over a 2-3 day period and then exposing the mature pathogen to the antifungals. This was done by cutting wells into the lawned agar, and removing the agar and filling the wells with cream.

The fungicidal test results are shown in FIGS. 22-28 and Tables 17-23 below.

TABLE 17

Fungicidal Test (FIG. 22)
Pathogen: *Trichophyton mentagrophytes*

| Position | Agent | Size of Clearance (mm) |
|---|---|---|
| 12:00 | AMYCOT ® 12.5% cream | 6 |
| 3:00 | AMYCOT ® 12.5% cream + 1% terbinafine | 6 |
| 6:00 | AMYCOT ® 12.5% cream + 10% tolnaftate | 6 |
| 9:00 | AMYCOT ® 12.5% cream + 10% clotrimazole | 5 |

TABLE 18

Fungicidal Test (FIG. 23)
Pathogen: *Trichophyton rubrum*

| Position | Agent | Size of Clearance (mm) |
|---|---|---|
| 12:00 | AMYCOT ® 12.5% cream | 9 |
| 3:00 | AMYCOT ® 12.5% cream + 10% clotrimazole | 7 |
| 6:00 | AMYCOT ® 12.5% cream + 1% miconazole | 8 |
| 9:00 | Placebo | 0 |

TABLE 19

Fungicidal Test (FIG. 24)
Pathogen: *Trichophyton mentagrophytes*

| Position | Agent | Size of Clearance (mm) |
|---|---|---|
| 12:00 | AMYCOT ® 12.5% cream | 6 |
| 3:00 | AMYCOT ® 12.5% cream + 1% terbinafine | 5 |
| 6:00 | AMYCOT ® 12.5% cream + 10% tolnaftate | 5 |
| 9:00 | AMYCOT ® 12.5% cream + 10% clotrimazole | 4 |

TABLE 20

Fungicidal Test (FIG. 25)
Pathogen: *Trichophyton mentagrophytes*

| Position | Agent | Size of Clearance (mm) |
|---|---|---|
| 12:00 | AMYCOT ® 12.5% cream | 8 |
| 3:00 | AMYCOT ® 12.5% cream + 1% terbinafine | 7 |
| 6:00 | AMYCOT ® 12.5% cream + 10% tolnaftate | 5 |
| 9:00 | AMYCOT ® 12.5% cream + 10% clotrimazole | 4 |

TABLE 21

Fungicidal Test (FIG. 26)
Pathogen: *Trichophyton mentagrophytes*

| Position | Agent | Size of Clearance (mm) |
|---|---|---|
| 12:00 | AMYCOT ® 12.5% cream | 9 |
| 3:00 | AMYCOT ® 12.5% cream + 1% terbinafine | 4 |
| 6:00 | AMYCOT ® 12.5% cream + 10% tolnaftate | 5 |
| 9:00 | AMYCOT ® 12.5% cream + 10% clotrimazole | 5 |

TABLE 22

Fungicidal Test (FIG. 27)
Pathogen: *Candida albicans*

| Position | Agent | Size of Clearance (mm) |
|---|---|---|
| 12:00 | AMYCOT ® 12.5% cream | 8 |
| 3:00 | Daktarin (miconazole 2%) | 0 |
| 6:00 | Canesten (clotrimazole 1%) | 0 |
| 9:00 | AMYCOT ® 12% + clotrimazole 1% | 5 |

TABLE 23

Fungicidal Test (FIG. 28)
Pathogen: *Trichophyton rubrum*

| Position | Agent | Size of Clearance (mm) |
|---|---|---|
| 12:00 | AMYCOT ® 12.5% cream | 6 |
| 3:00 | 10% clotrimazole | 0 |
| 6:00 | 10% tolnaftate | 0 |
| 9:00 | 2% miconazole | 0 |

Figure 28:
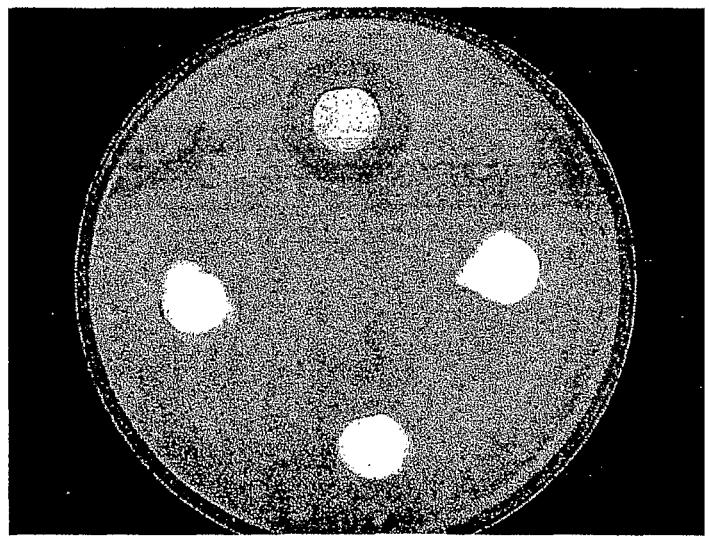
FIG. 28 shows *T. rubrum* fungicidal results using AMYCOT® and monographed actives.

The monographed actives in FIG. 28 are in an aqueous cream base as opposed to a spirit base which is normally used.

The results support that the present over-the-counter antifungals and monographed actives are fungi-static agents and not fungicides. FIGS. 22-28 and Tables 17-23 demonstrate that AMYCOT® is an efficacious fungicide, even when combined with monographed actives.

The combination of AMYCOT® with either miconazole or clotrimazole did not greatly reduce the efficacies of either. The combination increased the inhibitory effect (see FIGS. 17-21). This created a very effective broad spectrum product.

The combination of AMYCOT® with clotrimazole slightly inhibited the antifungal activity of AMYCOT® (see FIGS. 22-28), but the combination of AMYCOT® with miconazole had no great detrimental effects on the inhibitory or the fungicidal activity of the combination cream (see FIGS. 17-26).

The combination cream of AMYCOT® and miconazole was more efficacious as a broad spectrum product than either due to the inhibitory nature of miconazole and both the inhibitory and fungicidal activities of AMYCOT®.

The combination cream acted as an inhibitor and then "held its ground", while clearances achieved with miconazole alone became encroached by regrowth as in the case of the pathogen *T. mentagrophytes* (see FIG. 20).

It was also found that the combination cream AMYCOT® and 2% miconazole restricted regrowth of the pathogen after a clearance was made around the wells.

Example 11

Trials of *Arthrospira* on Various Skin Conditions

A subject had advanced athlete's foot, with deep lesions between the toes. The subject reported that itching caused by the fungus stopped within 15 minutes of first applying 12.5% w/w AMYCOT® cream. Inflammation reduced and in some cases disappeared completely in 12 hours. The lesions began closing within 24 hours and completely healed within 4-5 days.

These observations were repeated in the case of acne with subjects recording that the associated inflammation disappeared and that their skin returned to normal colour and became soft and pliable like new skin. The pustules also dried out.

It is the belief of the inventors that one or more biocidal agents (eg. chitinase, chitosanase, chitin deacetylase) interact synergistically with other components of *Arthrospira* to give rise to the therapeutic effects. The itching in fungal infections is an indication of the release of digestive enzymes or metabolites from the fungi. Once normal fungal metabolism is disrupted as the cell wall is disrupted, itching ceases.

Similar results were obtained when using the cream for conditions unrelated to fungus, on dry and cracked heels and elbows, rosacea, eczema, sun damaged skin and psoriasis. Subjects reported almost immediate relief from itching in dermatitis.

Example 12

Antifungal Activity of Stressed *Arthrospira* Using "Unprocessed" Powder

Example 5 supported that commercial preparations of dried *Arthrospira* were likely to have some level of antifungal activity without requiring an additional stressing step or post-harvest processing step such as filament disruption. Example 12 further supports this finding.

A dried preparation of *Arthrospira maxima* was sourced from a commercial grower. The preparation was blended with an over-the-counter aqueous cream at a concentration of 12.5% w/w without further processing, and was tested for antifungal activity against *T. mentagrophytes, T. rubrum* and *M. fructicola* (as described in Example 5).

Figure 31:
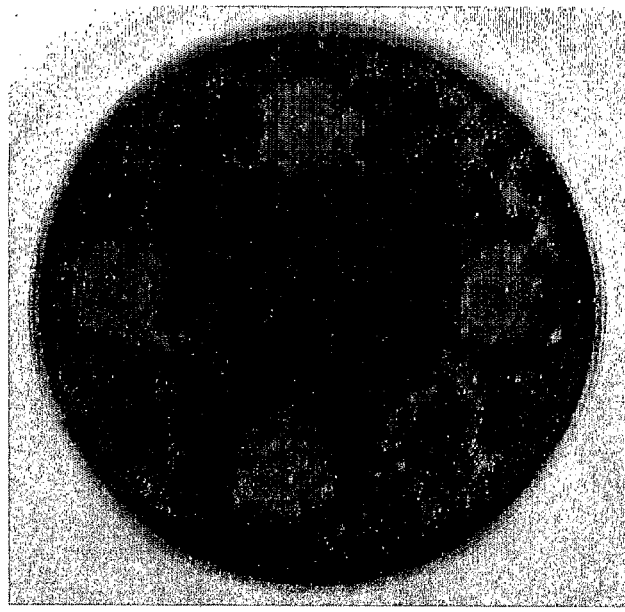
FIG. 31 shows antifungal activity of *Arthrospira* on *T. mentagrophytes;*

As seen in FIG. 31, the cream produced a clearance against *T. mentagrophytes* at the 12, 3, 6 and 9 o'clock positions.

Figure 32:
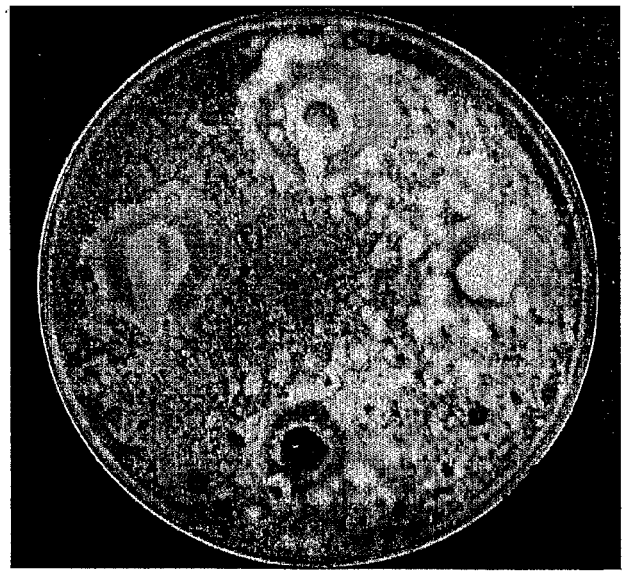
FIG. 32 shows antifungal activity of *Arthrospira* on *T. rubrum;*

As seen in FIG. 32, the cream produced a clearance against *T. rubrum* at the 6 o'clock position.

Figure 33:
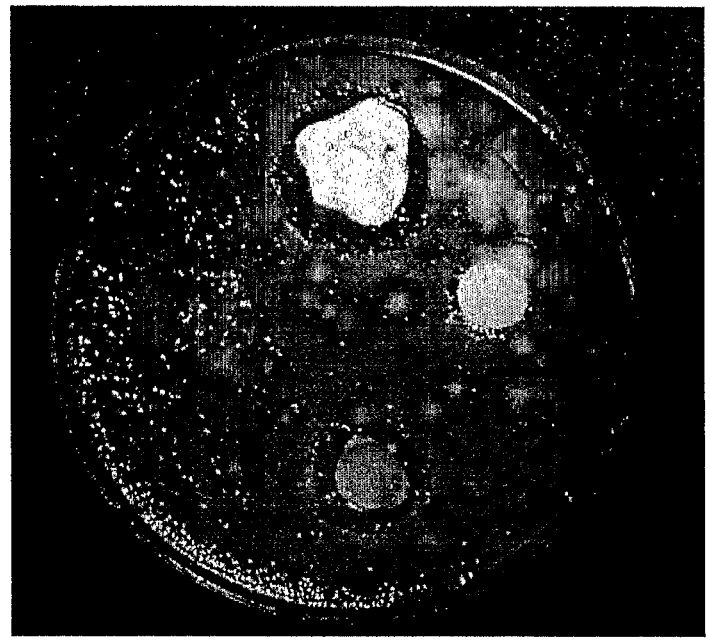
FIG. 33 shows antifungal activity of *Arthrospira* on *M. fructicola;*.

As seen in FIG. 33, the cream produced a clearance against *M. fructicola* at the 6 o'clock position.

These findings support that post-harvest steps such as explosive decompression, dry freezing, decolourisation and milling need not be carried out in order to produce *Arthrospira* having fungicidal activity.

Example 13

Antifungal Activity of *Arthrospira* Not Explosively Decompressed

This example further supports that the post-harvesting step of explosive decompression (potentiation) is not required in order to produce *Arthrospira* having fungicidal activity.

A dry preparation of *Arthrospira maxima* was sourced from a commercial grower. In one instance, dried *Arthrospira* was disrupted by explosive decompression (potentiated)

using the method described in New Zealand Patents No. 328013 and No. 328740. The *Arthrospira* was re-hydrated, decolourised, dried and milled to form a dry "premix powder". The premix powder was then suspended in a suitable carrier (12.5%) and will be referred to as "potentiated AMY-COT®".

In another instance, the preparation excluded the explosive decompression method described in New Zealand Patents No. 328013 and No. 328740, and this preparation will be referred to as "original AMYCOT®".

Figure 34:
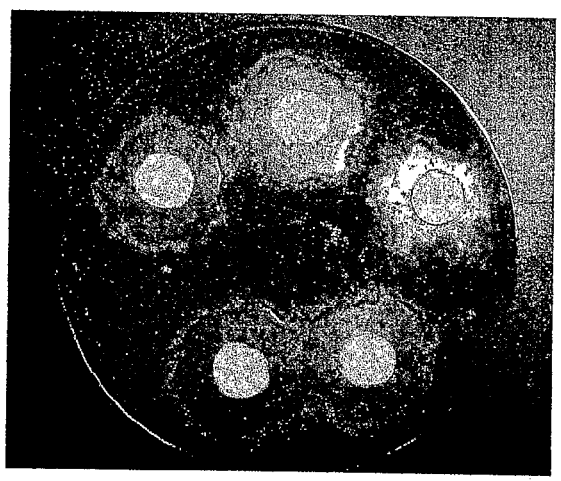
FIG. 34 shows antifungal activity of "potentiated AMYCOT®" and "original AMYCOT®" on *Alternaria* sp.

As seen in FIG. 34, both "original AMYCOT®" and "potentiated AMYCOT®" produced almost equal clearances against *Alternaria* sp. at the 12 and 7 o'clock positions, respectively. Hence, explosive decompression is not an essential post-harvest step for producing *Arthrospira* having fungicidal activity.

It will be further appreciated that many changes can be made to the compositions, methods of use and preparation exemplified above without departing from the broad ambit and scope of the invention.

The term "comprise" and variants of the term such as "comprises" or "comprising" are used herein to denote the inclusion of a stated integer or stated integers but not to exclude any other integer or any other integers, unless in the context or usage an exclusive interpretation of the term is required.

Any reference to publications cited herein is not an admission that the disclosures constitute common general knowledge in Australia.

The invention claimed is:

1. A method for preparing a topical *Arthrospira*-based composition, said method comprising the steps of:
    (1) growing *Arthrospira*;
    (2) as a separate step, physiologically stressing the *Arthrospira* by a stressing technique selected from the group consisting of: depriving nutrients, depriving light, dehydrating and removing up to 80% of liquid within which the *Arthrospira* is being grown until substantially all of the *Arthrospira* enters an anabiotic state, but not freeze drying the *Arthrospira*, and obtaining stressed *Arthrospira*; and
    (3) combining a fungicidally or bactericidally effective amount of the stressed *Arthrospira* with a carrier, a solvent, a base or an excipient suitable for topical administration to the subject to form a the topical *Arthrospira*-based composition comprising at least 0.01% weight/weight stressed *Arthrospira*, and wherein the stressed *Arthrospira* of the composition comprises a filament material selected from the group consisting of: intact *Arthrospira* filaments, segments of *Arthrospira* filaments and disrupted *Arthrospira* filaments.

2. A topical *Arthrospira*-based composition prepared by the method of claim 1.

3. A method for preparing a topical fungicide or bactericide *Arthrospira*-based composition, said method comprising the steps of:
    (1) growing *Arthrospira*;
    (2) as a separate step, physiologically stressing the *Arthrospira* by removing up to about 80% of liquid within which the *Arthrospira* is being grown until substantially all of the *Arthrospira* enters an anabiotic state;
    (3) washing the stressed *Arthrospira* of step (2) in order to remove contaminants;
    (4) drying the washed *Arthrospira* of step (3); and to obtain a dried stressed *Arthrospira*, wherein the *Arthrospira* has not been freeze dried
    (5) combining a fungicidally or bactericidally effective amount of the dried stressed *Arthrospira* with a carrier, a solvent, a base or an excipient suitable for topical administration to a subject to form a the topical *Arthrospira*-based composition comprising at least 5% weight/weight stressed *Arthrospira*, and wherein the *Arthrospira* of the composition comprises a filament material selected from the group consisting of: intact *Arthrospira* filaments, segments of *Arthrospira* filaments and disrupted *Arthrospira* filaments.

4. A topical fungicide or bactericide *Arthrospira*-based composition prepared by the method of claim 3.

5. A topical *Arthrospira*-based composition comprising a fungicidally effective amount of physiologically stressed *Arthrospira*, which is in an anabiotic state, and a carrier, a solvent, a base or an excipient suitable for topical administration, wherein the composition comprises at least 0.01% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried, and wherein the stressed *Arthrospira* of the composition comprises a filament material selected from the group consisting of: intact *Arthrospira* filaments, segments of *Arthrospira* filaments and disrupted *Arthrospira* filaments.

6. A method for preventing or treating a topical fungal infection or infestation of a subject, said method comprising the step of topically administering to the subject a composition comprising a fungicidally effective amount of physiologically stressed *Arthrospira*, which is in an anabiotic state, and a carrier, a solvent, a base or an excipient suitable for topical administration to a subject, wherein the composition comprises at least 0.5% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried and wherein the stressed *Arthrospira* of the composition comprises a filament material selected from the group consisting of: intact *Arthrospira* filaments, segments of *Arthrospira* filaments and disrupted *Arthrospira* filaments.

7. The method of claim 6 further comprising the step of initially identifying a subject in need of such treatment or requiring such prevention.

8. The method of claim 6, wherein the subject is a human, an animal, an agricultural or horticultural product, soil or a man-made structure.

9. A method for preparing a topical fungicidal *Arthrospira*-based composition, said method comprising the steps of:
    (1) growing *Arthrospira*;
    (2) as a separate step, physiologically stressing the *Arthrospira* by a stressing technique selected from the group consisting of: depriving nutrients, depriving light, dehydrating, and removing up to 80% of liquid within which the *Arthrospira* is being grown until substantially all of the *Arthrospira* enters an anabiotic state, wherein the *Arthrospira* has not been freeze dried; and
    (3) combining a fungicidally effective amount of the stressed *Arthrospira* with a carrier, a solvent, a base or an excipient suitable for topical administration to a subject to form the topical fungicidal *Arthrospira*-based composition comprising at least 5% weight/weight stressed

*Arthrospira*, and wherein the stressed *Arthrospira* of the composition comprises a filament material selected from the group consisting of: intact *Arthrospira* filaments, segments of *Arthrospira* filaments and disrupted *Arthrospira* filaments.

10. A topical fungicidal *Arthrospira*-based composition comprising:
   a combination of physiologically stressed *Arthrospira*, which is in an anabiotic state, at least one fungi-static agent, and a carrier, a solvent, a base or an excipient suitable for topical administration, wherein the composition comprises at least 0.01% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried, and wherein the stressed *Arthrospira* of the composition comprises a filament material selected from the group consisting of: intact *Arthrospira* filaments, segments of *Arthrospira* filaments and disrupted *Arthrospira* filaments.

11. The topical fungicidal composition of claim 10, wherein the at least one fungi-static agent is selected from the group consisting of: terbinafine, bifonazole, clotrimazole, miconazole, econazole, ketoconazole, and tolnaftate.

12. A method for preventing or treating a topical fungal infection or infestation of a subject, said method comprising the step of:
   topically administering to the subject a composition comprising a fungicidally effective amount of physiologically stressed *Arthrospira*, which is in an anabiotic state, at least one fungi-static agent, and a carrier, a solvent, a base or an excipient suitable for topical administration to a subject, wherein the composition comprises at least 5% weight/weight stressed *Arthrospira*, wherein the physiological stressing is induced using a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried and wherein the stressed *Arthrospira* of the composition comprises a filament material selected from the group consisting of: intact *Arthrospira* filaments, segments of *Arthrospira* filaments and disrupted *Arthrospira* filaments.

13. The method of claim 12, wherein the at least one fungi-static agent is selected from the group consisting of: terbinafine, bifonazole, clotrimazole, miconazole, econazole, ketoconazole, and tolnaftate.

14. A topical bactericidal *Arthrospira*-based composition comprising:
   a bactericidally effective amount of physiologically stressed *Arthrospira*, which is in an anabiotic state, and a carrier, a solvent, a base or an excipient suitable for topical administration to a subject, wherein the composition comprises at least 5% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried, and wherein the stressed *Arthrospira* of the composition comprises a filament material selected from the group consisting of: intact *Arthrospira* filaments, segments of *Arthrospira* filaments and disrupted *Arthrospira* filaments.

15. A method for preventing or treating a topical bacterial infection or infestation of a subject, said method comprising:
   topically administering to the subject a composition comprising a bactericidally effective amount of physiologically stressed *Arthrospira*, which is in an anabiotic state, and a carrier, a solvent, a base or an excipient suitable for topical administration to a subject, wherein the composition comprises at least 5% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state wherein the *Arthrospira* has not been freeze dried, and wherein the stressed *Arthrospira* of the composition comprises a filament material selected from the group consisting of: intact *Arthrospira* filaments, segments of *Arthrospira* filaments and disrupted *Arthrospira* filaments.

16. The method of claim 15 further comprising the step of initially identifying a subject in need of such treatment or requiring such prevention.

17. The method of claim 15, wherein the topical bacterial infection is caused by *Propionibacterium acne*.

18. The method of claim 15, wherein the subject is human.

19. A method for preparing a topical bactericidal *Arthrospira*-based composition, said method comprising the steps of:
   (1) growing *Arthrospira*;
   (2) as a separate step, physiologically stressing the *Arthrospira* by a stressing technique selected from the group consisting of: depriving nutrients, depriving light, dehydrating, and removing up to 80% of liquid within which the *Arthrospira* is being grown until substantially all of the *Arthrospira* enters an anabiotic state to obtain a dried stressed *Arthrospira*, wherein the *Arthrospira* has not been freeze dried; and
   (3) combining a bactericidally effective amount of the stressed *Arthrospira* with a carrier, a solvent, a base or an excipient suitable for topical administration to a subject to form the topical bactericidal *Arthrospira*-based composition comprising at least 5% weight/weight stressed *Arthrospira*, and wherein the stressed *Arthrospira* of the composition comprises a filament material selected from the group consisting of: intact *Arthrospira* filaments, segments of *Arthrospira* filaments and disrupted *Arthrospira* filaments.

20. A topical *Arthrospira*-based composition for treating a defect of the skin of a mammal, said composition comprising:
   a fungicidally or bactericidally effective amount of physiologically stressed *Arthrospira*, which is in an anabiotic state, and a carrier, a solvent, a base or an excipient suitable for topical administration to a subject, wherein the composition comprises at least 5% weight/weight stressed *Arthrospira*, wherein the physiological stressing is induced by a stressing technique selected from the group consisting of: depriving nutrients, depriving light, dehydrating, and removing up to 80% of liquid within which the *Arthrospira* is being grown until substantially all of the *Arthrospira* enters the anabiotic state, wherein the *Arthrospira* has not been freeze dried, and wherein the stressed *Arthrospira* of the composition comprises a filament material selected from the group consisting of:

intact *Arthrospira* filaments, segments of *Arthrospira* filaments and disrupted *Arthrospira* filaments.

21. A method of treating a defect of the skin of a mammal, said method comprising the step of topically administering to the mammal a composition comprising:

a fungicidally or bactericidally effective amount of physiologically stressed *Arthrospira*, which is in an anabiotic state, and a carrier, a solvent, a base or an excipient suitable for topical administration to a subject, wherein the composition comprises at least 5% weight/weight stressed *Arthrospira, wherein the physiological stressing is induced by a stressing technique selected from the group consisting of: depriving nutrients, depriving light, dehydrating, and removing up to* 80% of liquid within which the *Arthrospira* is being grown until substantially all of the *Arthrospira* enters the anabiotic state wherein the *Arthrospira* has not been freeze dried, and wherein the stressed *Arthrospira* of the composition comprises a filament material selected from the group consisting of: intact *Arthrospira* filaments, segments of *Arthrospira* filaments and disrupted *Arthrospira* filaments.

22. The method of claim 21 further comprising the step of initially identifying a mammal in need of such treatment or requiring such prevention.

23. The method of claim 21, wherein the skin defect is selected from the group consisting of a pit, acne damage, rosacea, a reddened area, a crack, a burn, a blister, psoriasis, eczema, scaling, wrinkles, a papule, a stomatitis, a lesion, a pustule, a wound, cradle cap, diaper rash, an ulcer, a cold sore, shaving rash, chicken pox, dermatitis, and cracked heels and elbows.

24. The method of claim 1, wherein the *Arthrospira* is *A. maxima*.

* * * * *

UNITED STATES PATENT AND TRADEMARK OFFICE
CERTIFICATE OF CORRECTION

PATENT NO. : 8,808,706 B2
APPLICATION NO. : 11/718247
DATED : August 19, 2014
INVENTOR(S) : Kelvin Winston Duncan et al.

Page 1 of 3

It is certified that error appears in the above-identified patent and that said Letters Patent is hereby corrected as shown below:

In the Specification,

COLUMN 5
Line 15, delete "Antifunal" and insert --Antifungal--

COLUMN 13
Lines 12-15, delete the entire heading:
"Antibacterial Activity of Stressed *Arthrospira* on *Propionibacterium acne* Respirometry showed that AMYCOT® has antibacterial activity against *P. acne*."

and replace with new heading:
--Antibacterial Activity of Stressed *Arthrospira* on *Propionibaterium acne*-- and insert the following sentence under new heading:
--Respirometry showed that AMYCOT® has antibacterial activity against *P. acne*.--

COLUMN 19
Line 9, Table 13, insert --1-- under "Size of Clearance" column for 9:00 position In the Claims, COLUMN 23
Line 46, delete "to form a the topical" and insert --to form the topical--

COLUMN 23
Line 65, delete "step (3); and to obtain" and insert --step (3) to obtain--

Signed and Sealed this
Third Day of February, 2015

Michelle K. Lee
*Deputy Director of the United States Patent and Trademark Office*

COLUMN 23
Line 67, delete "freeze dried" and insert --freeze dried; and--

COLUMN 24
Line 4, delete "to form a the topical" and insert --to form the topical--

COLUMN 24
Line 61, after the word "state" delete ","

COLUMN 25
Line 38, delete "is induced using a stressing" and insert --is induced by a stressing--

COLUMN 25
Lines 60-63, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Lines 12-15, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Lines 59-62, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Line 64, after the word "state" delete ","

COLUMN 27
Lines 11-14, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

UNITED STATES PATENT AND TRADEMARK OFFICE
CERTIFICATE OF CORRECTION

PATENT NO.       : 8,808,706 B2
APPLICATION NO.  : 11/718247
DATED            : August 19, 2014
INVENTOR(S)      : Kelvin Winston Duncan et al.

It is certified that error appears in the above-identified patent and that said Letters Patent is hereby corrected as shown below:

In the Specification,

COLUMN 5
Line 15, delete "Antifunal" and insert --Antifungal--

COLUMN 13
Lines 12-15, delete the entire heading:
"Antibacterial Activity of Stressed *Arthrospira* on *Propionibacterium acne* Respirometry showed that AMYCOT® has antibacterial activity against *P. acne.*"

and replace with new heading:
--Antibacterial Activity of Stressed *Arthrospira* on *Propionibacterium acne*-- and insert the following sentence under new heading:
--Respirometry showed that AMYCOT® has antibacterial activity against *P. acne.*--

COLUMN 19
Line 9, Table 13, insert --1-- under "Size of Clearance" column for 9:00 position In the Claims, COLUMN 23
Line 46, delete "to form a the topical" and insert --to form the topical--

This certificate supersedes the Certificate of Correction issued February 3, 2015.

Signed and Sealed this
Fifth Day of May, 2015

Michelle K. Lee
*Director of the United States Patent and Trademark Office*

COLUMN 23
Line 65, delete "step (3); and to obtain" and insert --step (3) to obtain--

COLUMN 23
Line 67, delete "freeze dried" and insert --freeze dried; and--

COLUMN 24
Line 4, delete "to form a the topical" and insert --to form the topical--

COLUMN 24
Line 61, after the word "state" delete ","

COLUMN 25
Line 38, delete "is induced using a stressing" and insert --is induced by a stressing--

COLUMN 25
Lines 60-63, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Lines 12-15, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Lines 59-62, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--

COLUMN 26
Line 64, after the word "state" delete ","

COLUMN 27
Lines 11-14, delete "*wherein the physiological stressing is induced by a stressing technique selected from the group consisting of: depriving nutrients, depriving light, dehydrating, and removing up to*"

and insert

--wherein the physiological stressing is induced by a stressing technique selected from the group consisting of: depriving nutrients, depriving light, dehydrating, and removing up to--